United States Patent
Abbaszadegan et al.

(10) Patent No.: US 6,395,517 B1
(45) Date of Patent: *May 28, 2002

(54) METHODS AND KITS FOR DETECTION OF CRYPTOSPORIDIUM PARVUM

(75) Inventors: Morteza Abbaszadegan, Swansea; George Dominic Di Giovanni, Fairview Heights, both of IL (US); Mark William LeChevallier, Voorhees, NJ (US)

(73) Assignee: American Water Works Company, Inc., Voorhees, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/618,932

(22) Filed: Jul. 18, 2000

Related U.S. Application Data

(63) Continuation of application No. 09/183,245, filed on Oct. 30, 1998, now Pat. No. 6,153,411.

(51) Int. Cl.$^7$ ............... C12Q 1/68; C12P 19/34; C07H 21/00; C07H 21/04
(52) U.S. Cl. ............. 435/91.2; 435/6; 435/91.1; 536/22.1; 536/23.1; 536/24.1; 536/24.2; 536/24.3; 536/24.33
(58) Field of Search .............. 435/6, 91.1, 91.2; 536/22.1, 23.1, 24.1, 242, 24.3, 24.31, 24.32, 24.33

(56) References Cited

U.S. PATENT DOCUMENTS

| | | |
|---|---|---|
| 3,996,345 A | 12/1976 | Ullman et al. |
| 4,018,886 A | 4/1977 | Giaever |
| 4,230,685 A | 10/1980 | Senyei et al. |
| 4,351,760 A | 9/1982 | Khanna et al. |
| 4,415,732 A | 11/1983 | Caruthers et al. |
| 4,458,066 A | 7/1984 | Caruthers et al. |
| 4,683,195 A | 7/1987 | Mullis et al. |
| 4,683,202 A | 7/1987 | Mullis |
| 4,725,677 A | 2/1988 | Köster et al. |
| 4,957,858 A | 9/1990 | Chu et al. |
| 4,965,188 A | 10/1990 | Mullis et al. |
| 4,980,460 A | 12/1990 | Molko et al. |
| 4,997,928 A | 3/1991 | Hobbs, Jr. |
| 5,188,934 A | 2/1993 | Menchen et al. |
| 5,231,191 A | 7/1993 | Woo et al. |
| 5,409,818 A | 4/1995 | Davey et al. |
| 5,437,990 A | 8/1995 | Burg et al. |
| 5,538,848 A | 7/1996 | Livak et al. |
| 5,556,774 A | 9/1996 | Wiedenmann et al. |
| 5,591,434 A | 1/1997 | Jenkins et al. |
| 5,643,772 A | 7/1997 | Petersen et al. |
| 5,665,352 A | 9/1997 | Blehaut et al. |
| 5,690,825 A | 11/1997 | Parton |
| 5,691,146 A | 11/1997 | Mayrand |
| 5,693,472 A | 12/1997 | Steele et al. |
| 5,750,496 A | 5/1998 | Forney et al. |
| 5,770,368 A | 6/1998 | De Leon et al. |
| 6,153,411 A | * 11/2000 | Abbaszadegan et al. ... 435/91.2 |

FOREIGN PATENT DOCUMENTS

EP         0310 256 A2     4/1989

OTHER PUBLICATIONS

Agrawal et al., 1990, Nucleic Acids Res. 18:5419–5423.
Basu et al., 1993, Biochemistry 32:4708–4718.
Beaucage and Iyer, 1992, Tetrahedron 48:2223–2311.
Bird et al., 1988, Science 242:423–426.
Bukhari et al., 1997, Abstract, Proceedings of The Water Quality Technology Conference, American Water Works Association, Denver, Co.
Campbell, et al., 1992, Appl. Environ. Microbiol. 58:3488–3493.
Campbell et al., 1997, In: International Symposium on Waterborne *Cryptosporidium,* Fricker et al., eds., American Water Works Association, Newport Beach, CA.
Clegg et al., 1993, Proc. Natl. Acad. Sci USA 90:2994–2998.
Deng et al., 1997, Appl. Environ. Microbiol. 63:3134–3138.
Deng and Cliver, 1998, App. and Env. Microbiol. 5:1954–1957.
Di Giovanni et al., 1997, Proceedings of the American Water Works Assoc., Water Quality Tech. Conf., Denver, CO.
Di Giovanni et al., 1998, Porc. Amer. Water Works Assoc. Water Qual. Tech. Conf. in San Diego, CA, Amer. Water Works Assoc., Denver, CO.
Dupont et al., 1995, N. Eng. J. Med. 332:855–859.
Filkorn et al., 1994, Zentralbl. Hyg. Unweltmed 195:489–494.
Heid et al., 1996, Genome Res. 6:986–994.
Houston et al., 1988, Proc. Natl. Acad. Sci. USA 85:5879–5883.
Khramtsov et al., 1995, J. Euk. Microbiol. 42:416–422.
Khramtsov et al, 1997, Bioch. and Bioph. Res. Comm. 230:164–166.
LeChevallier and Norton, 1995, J. Am. Water Works Assoc. 87:54–68.
LeChavallier et al., 1991, Appl. Environ. Microbiol. 57:2610–2616.
LeChevallier et al., 1996, Proc. Amer. Water Works Assoc. Water Qual. Tech. Conf. in Boston, MA, Amer. Water Works Assoc., Denver, CO.
LeChevallier et al., 1991, App and Env. Micr. 57:2617–2621.
Lee et al., 1993, Nucleic Acids Res. 21:3761–3766.
Livak et al., 1995, Guidelines for Designing TaqMan™ Fluorgenic probes for 5' Nuclease Assays, In: *Perkin Elmer Research News,* Applied Biosystems Division, Foster City, CA.

(List continued on next page.)

*Primary Examiner*—Jeffrey Siew
(74) *Attorney, Agent, or Firm*—Akin, Gump, Strauss, Hauer & Feld, L.L.P.

(57) ABSTRACT

The invention relates to methods for the sensitive, specific, and, preferably, quantitative detection of *C. parvum* oocysts in aqueous samples.

23 Claims, 11 Drawing Sheets

OTHER PUBLICATIONS

Marshall, 1975, Histochemical J. 7:299–303.

Ozaki and McLaughlin, 1992, Nucleic Acids Res. 20:5205–5214.

Rochelle et al., 1997, Appl. Environ. Microbiol. 63:2029–2037(427–1).

Stinear et al., 1996, Appl. Environ. Microbiol. 62:3385–3390(427–1).

U.S. Environmental Protection Agency ICR, 1996, Fed. Regist. 61:24354–24388 (427–1).

Upton et al., 1995, J. Clin. Microbiol. 33:371–375(427–1).

Wagner–Weining and Kimmig, 1995, Appl. Environ. Microbiol. 61:4514–4516(427–1).

Woods et al., 1995, FEMS Microbiol. Lett. 128:89–93(427–1).

Wu et al., 1994, Anal. Biochem. 218:1–13(427–1).

Zhu et al., J. of Infectious Diseases 177:1443–1446(427–1).

* cited by examiner

FIG. 1A

5'
701  AGAGAAAGAA TAGAGGTATG GATTAACCA CAAATGCTAG AGCTTTAAGA AGACTCAGAA
     TCTCTTTCTT ATCTCCATAC CTAAATTGGT GTTTACGATC TCGAAATTCT TCTGAGTCTT

CTCAATGCGA GCGTGCAAAG AGAACTTTGT CATCTTCTAC TCAAGCTACA ATTGAGTTAG
     GAGTTACGCT CGCACGTTTC TCTTGAAACA GTAGAAGATG AGTTCGATGT TAACTCAATC

ATTCACTCTA TGAAGGTATT GATTATTCAG TTGCCATCAG TAGAGCTAGA TTCGAAGAAC
     TAAGTGAGAT ACTTCCATAA CTAATAAGTC AACGGTAGTC ATCTCGATCT AAGCTTCTTG

TCTGCGCTGA TTACTTCCGT GCAACTTTAG CTCCAGTTGA GAAAGTACTC AAGGATGCTG
     AGACGCGACT AATGAAGGCA CGTTGAAATC GAGGTCAACT CTTTCATGAG TTCCTACGAC

GTATGGACAA GAGATCTGTA CATGATGTTG TATTGGTTGG TGGTTCTACA CGTATTCCAA
     CATACCTGTT CTCTAGACAT GTACTACAAC ATAACCAACC ACCAAGATGT GCATAAGGTT

AGGTTCAGGC CTTGATTCAG GAATTCTTTA ACGGTAAAGA GCCATGCAAA GCAATCAATC
     TCCAAGTCCG GAACTAAGTC CTTAAGAAAT TGCCATTTCT CGGTACGTTT CGTTAGTTAG

CAGACGAAGC TGTTGCTTAT GGTGCTGCTG TACAAGCTGC TATCTTAAAT GGTGAGCAAT
     GTCTGCTTCG ACAACGAATA CCACGACGAC ATGTTCGACG ATAGAATTTA CCACTCGTTA

1001 CCTCTGCCGT ACAGGATCTC TTATTATTGG ATGTTGCTCC ATTATCACTC GGTTTAGAAA
     GGAGACGGCA TGTCCTAGAG AATAATAACC TACAACGAGG TAATAGTGAG CCAAATCTTT

```
CTGCTGGTGG TGTTATGACC AAGCTTATTG AACGTAATAC AACTATCCCA GCAAAGAAGA
GACGACCACC ACAATACTGG TTCGAATAAC TTGCATTATG TTGATAGGGT CGTTCTTCT

CACAAGTCTT CACTACTTAT GCTGATAACC AGAGTGGTGT CTTGATCCAA GTTTATGAGG
GTGTTCAGAA GTGATGAATA CGACTATTGG TCTCACCACA GAACTAGGTT CAAATACTCC

GTGAGAGAGC CATGACTAAG GATAACCATC TCCTCGGAAA GTTCCATCTT GATGGTATTC
CACTCTCTCG GTACTGATTC CTATTGGTAG AGGAGCCTTT CAAGGTAGAA CTACCATAAG

CACCAGCACC AAGAGGTGTA CCACAAATTG AAGTCACCTT TGATATTGAT GCTAATGGTA
GTGGTCGTGG TTCTCCACAT GGTGTTTAAC TTCAGTGGAA ACTATAACTA CGATTACCAT
```
1301
```
TCTTGAATGT GTCTGCTGTT GATAAGAGTA CTGGTAAGAG CAGCAAGATC ACTATTACTA
AGAACTTACA CAGACGACAA CTATTCTCAT GACCATTCTC GTCGTTCTAG TGATAATGAT

ACGATAAGGG TAGATTATCA AACGATATTG AACGTATGGT TAATGATGCT GAGAAATACA
TGCTATTCCC ATCTAATAGT TTGCTATAAC TTGCATACCA ATTACTACGA CTCTTTATGT

AGGGTGAGGA TGAGCAGAAC AGACTTAAGA TTGAGGCTAA GAACTCTTTG GAGAACTACC
TCCCACTCCT ACTCGTCTTG TCTGAATTCT AACTCCGATT CTTGAGAAAC CTCTTGATGG
```
1601
```
TCTATAACAT GAGGAACACC ATCCAAGAAC CAAAGGTTAA GGAAAAGCTT TCTCAATCTG
AGATATTGTA CTCCTTGTGG TAGGTTCTTG GTTTCCAATT CCTTTTCGAA AGAGTTAGAC
```

```
AAATTGATGA GGCTGAGAAG AAGATCAAGG ATGCTCTTGA CTGGCTCGAG CACAACCAAA
TTTAACTACT CCGACTCTTC TTCTAGTTCC TACGAGAACT GACCGAGCTC GTGTTGGTTT

CTGCTGAAAA GGACGAGTTT GAACATCAAC AAAAGGAGAT TGAAACTCAT ATGAATCCAC
GACGACTTTT CCTGCTCAAA CTTGTAGTTG TTTTCCTCTA ACTTTGAGTA TACTTAGGTG

TCATGATGAA GATCTACTCT GCTGAGGGTG GTATGCCAGG TGGAATGCCA GGTGGTATGC
AGTACTACTT CTAGATGAGA CGACTCCCAC CATACGGTCC ACCTTACGGT CCACCATACG

CAGGCGGTAT GCCAGGTGGA ATGCCAGGTG GTATGCCAGG TGGAATGCCA GGCGGTATGC
GTCCGCCATA CGGTCCACCT TACGGTCCAC CATACGGTCC ACCTTACGGT CCGCCATACG

CAGGTGGTAT GCCAGGTGGT ATGCCAGGTG GTATGCCAGG ATCTAATGGT CCAACTGTTG
GTCCACCATA CGGTCCACCA TACGGTCCAC CATACGGTCC TAGATTACCA GGTTGACAAC

AAGAGGTCGA CTAATTATTT TAGTCACCAA AAAAACTCAC TCAAAATGGA AAGTTAAGAA
TTCTCCAGCT GATTAATAAA ATCAGTGGTT TTTTTGAGTG AGTTTTACCT TTCAATTCTT

CTATTTACAC ACTTTCAATT TCTAGTTATT TTTTACCAAA ATAAGAAGAA AAGCACACTC
GATAAATGTG TGAAAGTTAA AGATCAATAA AAAATGGTTT TATTCTTCTT TTCGTGTGAG

TACCTTTAGG CTATATTTTC
ATGGAAATCC GATATAAAAG
```

1901

METHODS AND KITS FOR DETECTION OF CRYPTOSPORIDIUM PARVUM

CROSS REFERENCE TO RELATED APPLICATION

This application is a continuation of U.S. application Ser. No. 09/183,245, filed on Oct. 30, 1998, which issued on Nov. 28, 2000, as U.S. Pat. No. 6,153,411, the entire disclosure of which is incorporated by reference herein.

BACKGROUND OF THE INVENTION

*Cryptosporidium parvum* (phylum Apicomplexa) is a coccidian protozoan capable of parasitizing the intestinal tract of a variety of mammalian species. The protozoan is generally believed to be spread by an oral-fecal route, infecting the intestinal epithelia and, to a lesser extent, the extraintestinal epithelia causing severe diarrhea. *C. parvum* has been increasingly recognized as the causative agent of recent waterborne outbreaks of gastroenteritis.

Although usually self-limiting, the diarrheal disease can be prolonged and life threatening to the young and to the immunosuppressed. While first recognized as a veterinary pathogen, cryptosporidiosis has gained in importance with the spread of AIDS-related immunosuppression. Further, numerous outbreaks of cryptosporidiosis have been reported in the United States involving children attending day-care facilities (Jenkins et al., 1997, U.S. Pat. No. 5,591,434, which is incorporated by reference herein as if set forth in its entirety). The disease has also been implicated as having a significant role in the vicious cycle of malnutrition/diarrhea among children in developing countries.

In a recent study, the 50% infectious dose in normal immunocompetent individuals was determined to be 132 oocysts and as few as 30 oocysts caused infection (Dupont et al., 1995, N. Eng. J. Med. 332:855–859). At present, there does not appear to be any prophylactic therapy available to prevent this parasitic disease in humans or in animals (Jenkins et al., supra), and there is no effective chemotherapeutic treatment for cryptosporidiosis once the host has been infected.

*Cryptosporidium parvum* exists in nature in the form of environmentally resistant, thick-walled oocysts. The oocysts are known to remain viable for extended periods of time and are resistant to conventional water disinfection methods. Due to massive shedding of oocysts in the feces of infected animals or individuals and the robust nature of the oocysts, they are frequently present in raw surface water (LeChevallier et al., 1991, Appl. Environ. Microbiol. 56:1423–1428) and finished drinking water (LeChevallier and Norton, 1995, J. Am. Water Works Assoc. 87:54–68). Currently, the U.S. Environmental Protection Agency Information Collection Rule (ICR) mandates the use of the indirect fluorescent antibody (IFA) method for the detection of Cryptosporidium oocysts in water concentrates (U.S. Environmental Protection Agency, 1996, Fed. Regist. 61:24354–24388). While the IFA method does not distinguish between viable and nonviable oocysts, the use of fluorogenic vital dyes may distinguish between viable and nonviable oocysts (Campbell et al., 1992, Appl. Environ. Microbiol. 58:3488–3493). However, the use of these microscopic techniques is hampered by their labor-intensive, time-consuming nature, their inability to distinguish between human pathogenic *C. parvum* oocyst and the oocyst of animal pathogenic Cryptosporidium species, and the inability of the tests to differentiate infectious and non-infectious oocysts.

Oocyst resistance to chlorination, difficulties in effective methods for detection of the parasite, and a lack of effective treatment for cryptosporidiosis have contributed to the spread of the organism. Accordingly, the importance of prophylaxis by detection of the parasite in drinking water before it is ingested by the human host has given impetus to the development of methods for the effective detection of *C. parvum* in water samples.

Recently, various strategies have been combined with standard polymerase chain reaction assay (PCR) to detect the presence of viable *C. parvum* oocysts, including integration of in vivo excystation (Deng et al., 1997, Appl. Environ. Microbiol. 63:3134–3138; Filkhorn et al., 1994, Zentralbl. Hyg. Unweltmed. 195:489–494; Wagner-Weining and Kimmig, 1995, Appl. Environ. Microbiol. 61:4514–4516), and the use of reverse-transcriptase PCR (RT-PCR) for the detection of mRNA transcripts found only in viable oocysts (Rochelle et al., 1997, Appl. Environ. Microbiol. 63:2029–2037; Stinear et al., 1996, Appl. Environ. Microbiol. 62:3385–3390). Further, infectivity assessment by integrated cell culture-PCR (CC-PCR) has also been developed (Di Giovanni et al., 1997, Proceedings of the American Water Works Assoc., Water Quality Tech. Conf., Denver, CO; De Leon and Rochelle., 1998, U.S. Pat. No. 5,770,368; Rochelle et al., 1997, Appl. Environ. Microbiol. 63:2029–2037). However, although these prior art methods provide high specificity and sensitivity, they do not provide a quantitative measure of starting target nucleic acid copy numbers and, therefore, the prior art methods do not accurately measure the numbers of oocysts in the samples. Further, until the present invention, there is no report that CC-PCR has been successfully used to detect infectious *C. parvum* in environmental raw water samples.

Although there has been limited success in detection of oocysts in environmental raw water samples using PCR methods, CC-PCR detection of infectious *C. parvum* oocysts in environmental raw water samples has been hampered by, among other things, difficulties in: removing inhibitors of PCR, quantitation of organisms, ensuring that sufficient equivalent volume is assayed, removal of compounds cytotoxic to the cell culture, and ensuring that the process of collection and analysis does not inactivate the oocysts. Nonetheless, the detection of infectious *C. parvum* oocyst contamination in environmental raw water samples is important in raw-source water assessment for effective watershed management and also in enabling the evaluation of the efficiency and quality of drinking water treatment procedures. Therefore, while the methods of present invention can be used to detect infectious oocysts in finished drinking water to protect the public health, the procedures disclosed herein also permit the examination of, inter alia, raw water, process water, and waste streams which is of great value for understanding parasite occurrence and the efficacy of water treatment processes.

Further, the prior art PCR-based assays for *C. parvum* require confirmation that the parasite is infectious and/or that the DNA amplified is, indeed, the *C. parvum*-specific target sequence by complex methodologies requiring, inter alia, skilled persons trained in recombinant DNA techniques. For example, heat shocking the organisms followed by reverse transcriptase PCR (RT-PCR) has been used to detect viable organisms (De Leon and Rochelle, 1998, U.S. Pat. No. 5,770,368) (hereinafter the ’368 patent). That patent also teaches the alternative procedure of inoculating susceptible mammalian cells with a sample in order to detect infectious *C. parvum* by RT-PGR.

In either case, all PCR-based prior art methods require that the PCR amplification products be examined using recombinant DNA techniques to confirm that the *C. parvum* target nucleic acid sequence has, indeed, been specifically amplified. Typically, PCR amplification products are separated according to size on agarose gels and then the fragments are visualized by ethidium bromide-fluorescence staining under ultraviolet light to determine the presence of the appropriately-sized fragment as predicted by the primer pair used to amplify the target nucleic acid sequence. The actual sequence identity of the putative PCR fragment may be confirmed by Southern blot hybridization using a short internal DNA probe which complements the DNA expected in the PCR product and which is labeled so that it may be detected on the blot. Thus, when the target PCR product has been generated by the amplification reaction, the matching labeled probe will hybridize to it thereby confirming the product's identity. Alternatively, the putative PCR product may be cloned and sequenced by standard methods. Thus, the prior art methods require complex, time-consuming sample handling by a technician skilled in recombinant DNA methodology.

Moreover, none of the prior art PCR-based methods are quantitative and, therefore, those methods do not provide a measure of the contamination level of the water sample assayed. This is because PCR, although highly sensitive, does not measure the initial amount of target nucleic acid in a sample. Indeed, prior art assays which identify viable organisms in a sample require additional steps preceding PCR amplification, i.e., heat shocking and reverse transcriptase, which further hinder quantitation as well as increase the opportunity for operator error in the detection procedure. Further, heat shocking followed by RT-PCR may provide some information on viability but does not assess the infectivity of the oocysts. Additionally, RT-PCR requires a much longer processing time, increases the complexity and cost of the detection procedure, and may be hampered by interference from RNases present in the sample which may degrade the mRNA product thereby producing false negative results and allowing the parasite to go undetected. Therefore, there is a significant need in the art for a simple, efficient, and preferably quantitative method for detecting and/or quantifying this potentially lethal pathogen in water samples.

SUMMARY OF THE INVENTION

The invention relates to the specific and, preferably, quantitative detection of *C. parvum* oocysts in aqueous samples.

The invention includes a method useful for detecting a *Cryptosporidium parvum* organism m an aqueous sample. The method comprises the steps of (a) concentrating any *Cryptosporidium parvum* organism present in the sample by immunomagnetic separation;

(b) amplifying a target *Cryptosporidium parvum* nucleic acid present in the sample after step (a);

(c) detecting any amplified target nucleic acid formed in step (b) to detect a *Cryptosporidium parvum* organism in an aqueous sample.

In one aspect, the aqueous sample is selected from the group consisting of an environmental raw water sample, a backwash water sample, a process water sample, and a finished water sample.

In another aspect, the method further comprises infecting a susceptible mammalian cell culture with *Cryptosporidium parvum* organisms concentrated in step (a), and producing the *Cryptosporidium parvum* target nucleic acid prior to amplifying the target nucleic acid in step (b).

In preferred embodiments, the mammalian cell culture is selected from the group consisting of a HCT-8 cell culture, a CaCo-2 cell culture, and a MDBK cell culture.

In another aspect, the cell culture is incubated for a period of time from about 4 hours to about 72 hours following inoculation.

In yet another aspect, step (b) further comprises hybridizing any amplified target nucleic acid formed with a fluorescer-quencher oligonucleotide probe specific for said target *Cryptosporidium parvum* nucleic acid and measuring the level of fluorescence in the sample, wherein the level of fluorescence is quantitatively correlated to the amount of *Cryptosporidium parvum* oocysts in the sample.

In another aspect, the fluorescer molecule is attached to the 5' end of the oligonucleotide probe, and further wherein the fluorescer molecule is selected from the group consisting of a 6-carboxyfluorescein fluorescer molecule, a tetrachloro-6-carboxyfluorescein fluorescer molecule, a 2,7,-dimethoxy-4,5-dichloro-6-carboxyfluorescein fluorescer molecule, and a hexachloro-6-carboxyfluorescein fluorescer molecule.

In yet another aspect, the quencher molecule 6-carboxytetramethylrhodamine is attached to the 3' end of the oligonucleotide probe.

A method useful for quantitatively detecting a *Cryptosporidium parvum* organism in a sample is also included in the invention. The method comprises the steps of (a) concentrating any *Cryptosporidium parvum* organism in the sample by immunomagnetic separation;

(b) amplifying a target *Cryptosporidium parvum* nucleic acid;

(c) hybridizing any amplified target nucleic acid formed in step (b) with a fluorescer-quencher oligonucleotide probe specific for the target *Cryptosporidium parvum* nucleic acid; and (d) detecting any amplified target nucleic acid by quantitative sequence detection, wherein the level of fluorescence is correlated to the quantitative measure of the amount of *Cryptosporidium parvum* oocysts in the sample, to quantitatively detect a *Cryptosporidium parvum* organism in a sample.

In one aspect, the nucleic acid is DNA.

The invention also includes a method of quantitatively detecting a *Cryptosporidium parvum* organism in an aqueous sample. The method comprises the steps of (a) contacting a target *Cryptosporidium parvum* nucleic acid with polymerase chain reaction reagents specific for the target nucleic acid, the polymerase chain reaction reagents including at least two polymerase chain reaction primers, a polymerase enzyme, and an oligonucleotide probe, the oligonucleotide probe further comprising:

(i) a sequence capable of hybridizing to a portion of the target *Cryptosporidium parvum* nucleic acid wherein the portion is unique to *Cryptosporidium parvum;*

(ii) a fluorescer molecule attached to a first end of the oligonucleotide;

(iii) a quencher molecule attached to a second end of said oligonucleotide capable of substantially quenching the fluorescer molecule when the oligonucleotide is intact, wherein the fluorescer molecule becomes substantially unquenched when the oligonucleotide probe is cleaved by DNA polymerase during amplification of the *Cryptosporidium parvum* target nucleic acid; and (iv) a 3' end which is impervious to the 5'→3' extension activity of the DNA polymerase; and (b) amplifying the target *Cryptosporidium parvum* nucleic acid by thermal cycling, wherein the thermal cycling is sufficient to amplify the target nucleic acid; and (c) measuring the level of fluorescence in the sample subsequent to thermal cycling, and further wherein the level of fluorescence is correlated to the amount of *Cryptosporidium parvum* oocysts present in the sample, to quantitatively detect a *Cryptosporidium parvum* organism in an aqueous sample.

In preferred embodiments, the aqueous sample is selected from the group consisting of an environmental raw water sample, a backwash water sample, a process water sample, and a finished water sample.

In one aspect, the method further comprises concentrating any *Cryptosporidium parvum* organism present in the sample by immunomagnetic separation prior to step (a).

In another aspect, the method further comprises infecting a susceptible mammalian cell culture with any *Cryptosporidium parvum* organism concentrated by immunomagnetic separation and producing the *Cryptosporidium parvum* target nucleic acid prior to step (a).

The invention also includes a kit for detecting a *C. parvum* nucleic acid, the kit comprising a first nucleic acid having the sequence SEQ ID NO:2, and a second nucleic acid having the sequence SEQ ID NO:3.

In one aspect, the kit comprises an oligonucleotide probe complementary to at least a portion of a nucleic acid having the sequence of residues 1120–1465 of SEQ ID NO:1.

In another aspect, the oligonucleotide probe has the sequence SEQ ID NO:4.

BRIEF DESCRIPTIONS OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings:

FIG. 1 comprising FIGS. 1A, 1B, and 1C, is a diagram depicting a portion of the *Cryptosporidium parvum* hsp70 gene [SEQ ID NO:1]. The sequences indicated with a double-line represent the preferred forward and reverse PCR primers ([SEQ ID NO:2] and [SEQ ID NO:3], respectively) and the preferred oligonucleotide probe ([SEQ ID NO:4]). The sequences indicated by a single-line represent the forward and reverse PCR primers ([SEQ ID NO:5] and [SEQ ID NO:6]), respectively, of the '368 patent. The internal oligonucleotide probe sequence of the '368 patent, [SEQ ID NO:7], used for detection of the PCR amplification product, is also indicated by a single line.

Figure 5:
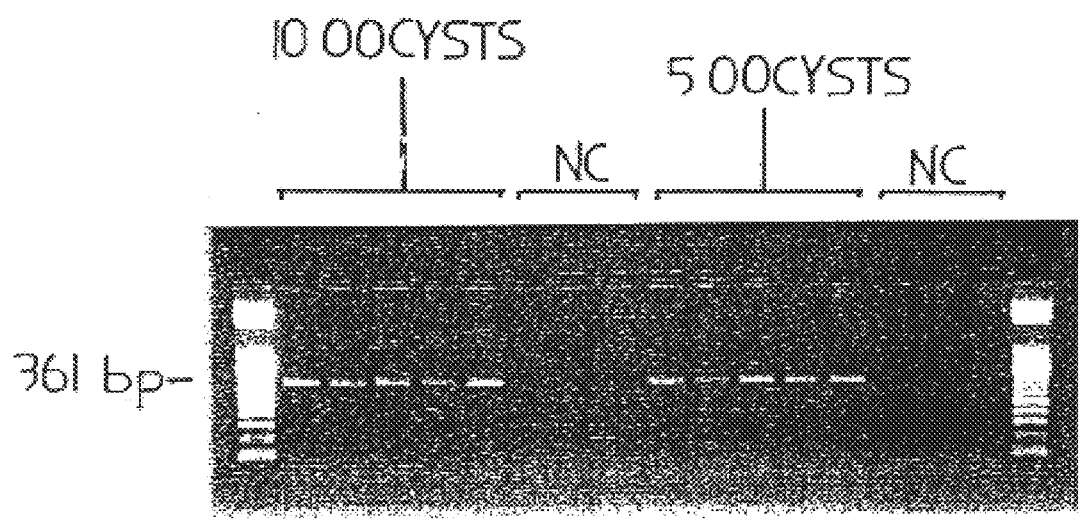

FIG. 5 is an image of a DNA gel depicting the agarose gel electrophoresis analysis of *C. parvum* PCR products using purified oocyst stocks (10 or 5 oocysts per reaction as indicated at the top of the figure). Each gel lane was loaded with 10 µl of one of the reaction mixtures for which the fluorescence endpoint is provided in Table 2. The gel was stained with ethidium bromide (EtBr) to detect the presence of the 361 bp PCR amplification product, and the intensity of the EtBr-stained band as determined by visual inspection was compared to the fluorescence intensity units (FIU) data depicted in Table 2. Lanes containing no *C. parvum* template DNA, indicated as negative control (NC) lanes, are also shown.

Figure 6:
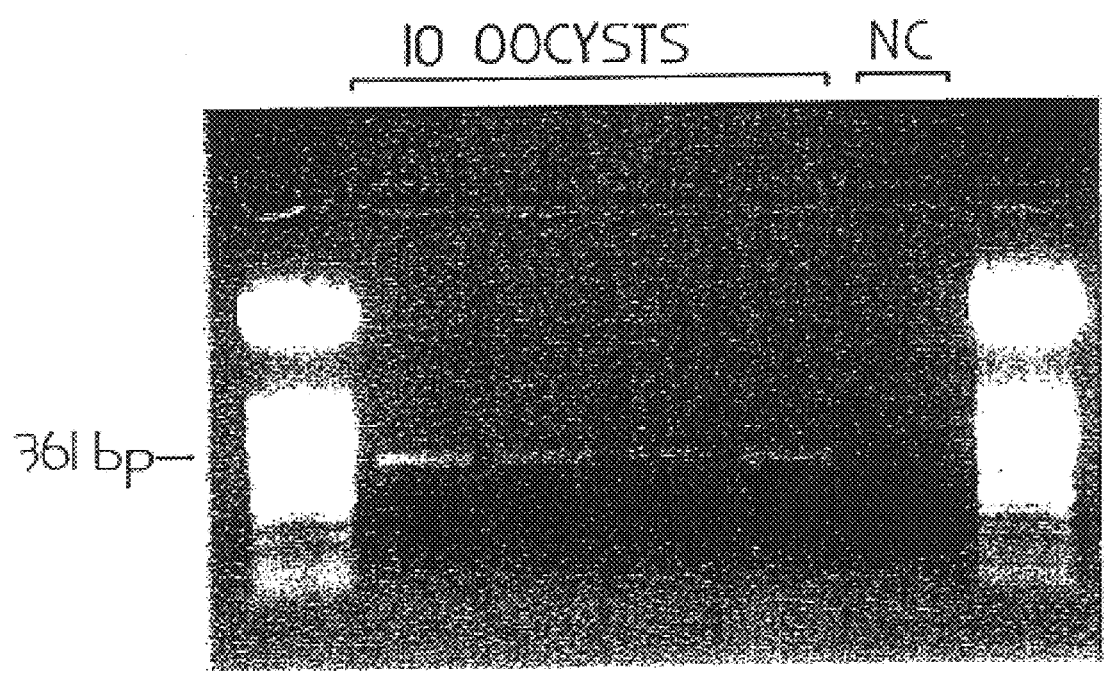

FIG. 6 is an image of an agarose gel depicting the electrophoresis analysis of *C. parvum* PCR products using IMS raw water concentrates seeded with purified oocyst stocks (10 oocysts per reaction as indicated at the top of the figure). Each gel lane was loaded with 15 µl of one of the reaction mixtures for which the fluorescence endpoint is illustrated in Table 3. The gel was stained with ethidium bromide (EtBr) to detect the presence-of the 361 bp PCR amplification product and the intensity of the EtBr-stained band as determined by visual inspection was compared to the FIU data depicted in Table 3. Lanes containing no *C. parvum* template DNA, indicated as negative control (NC) lanes, are also shown. The results of four replicates are depicted.

Figure 7A:
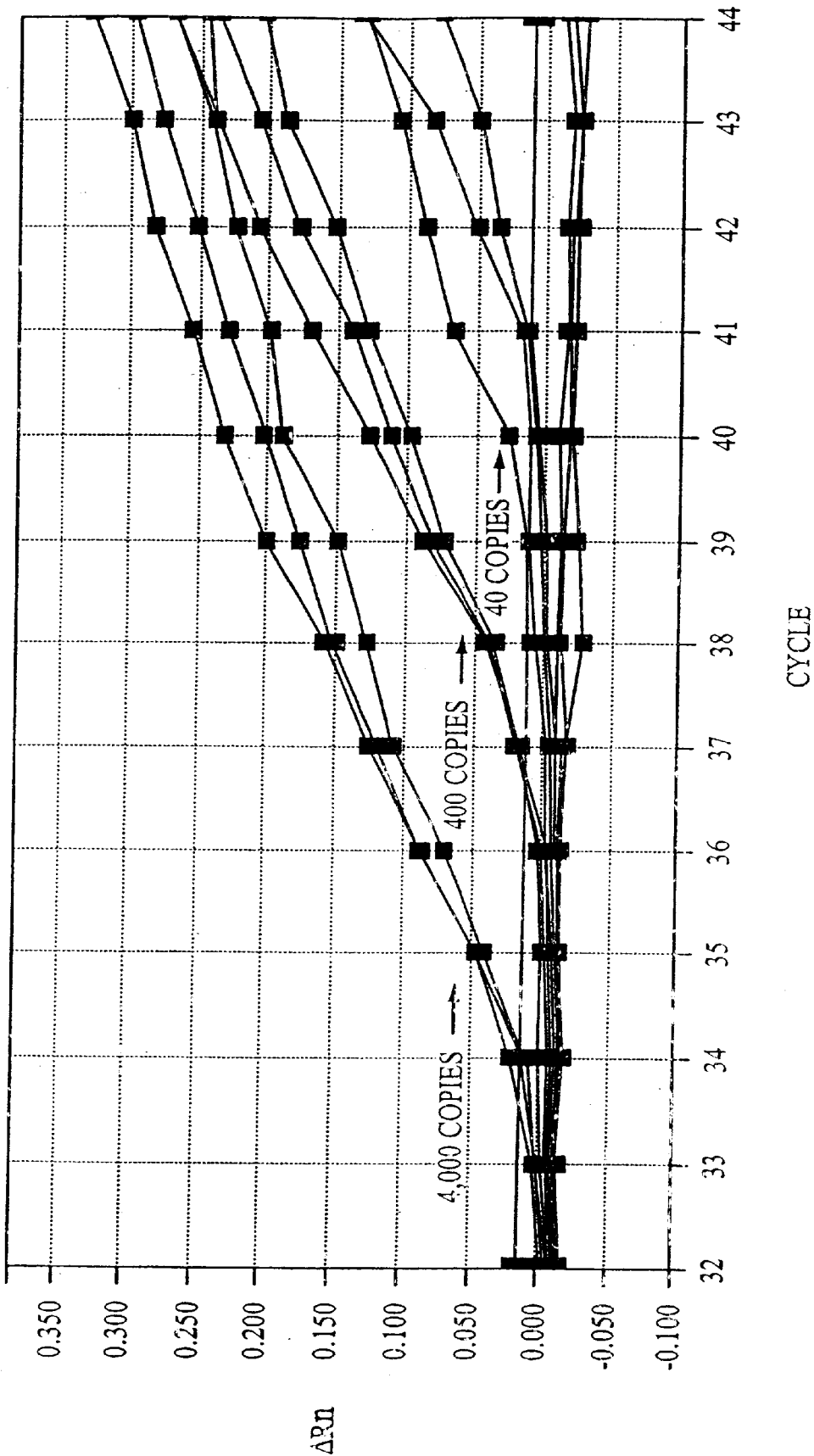

FIG. 7A is a graph depicting the detection and quantitation of *C. parvum* oocysts in a sample by QSD using the prior art primer pair and probe of the '368 patent (i.e., [SEQ ID NO:5], [SEQ ID NO:6], and [SEQ ID NO:7], respectively).

Figure 7B:
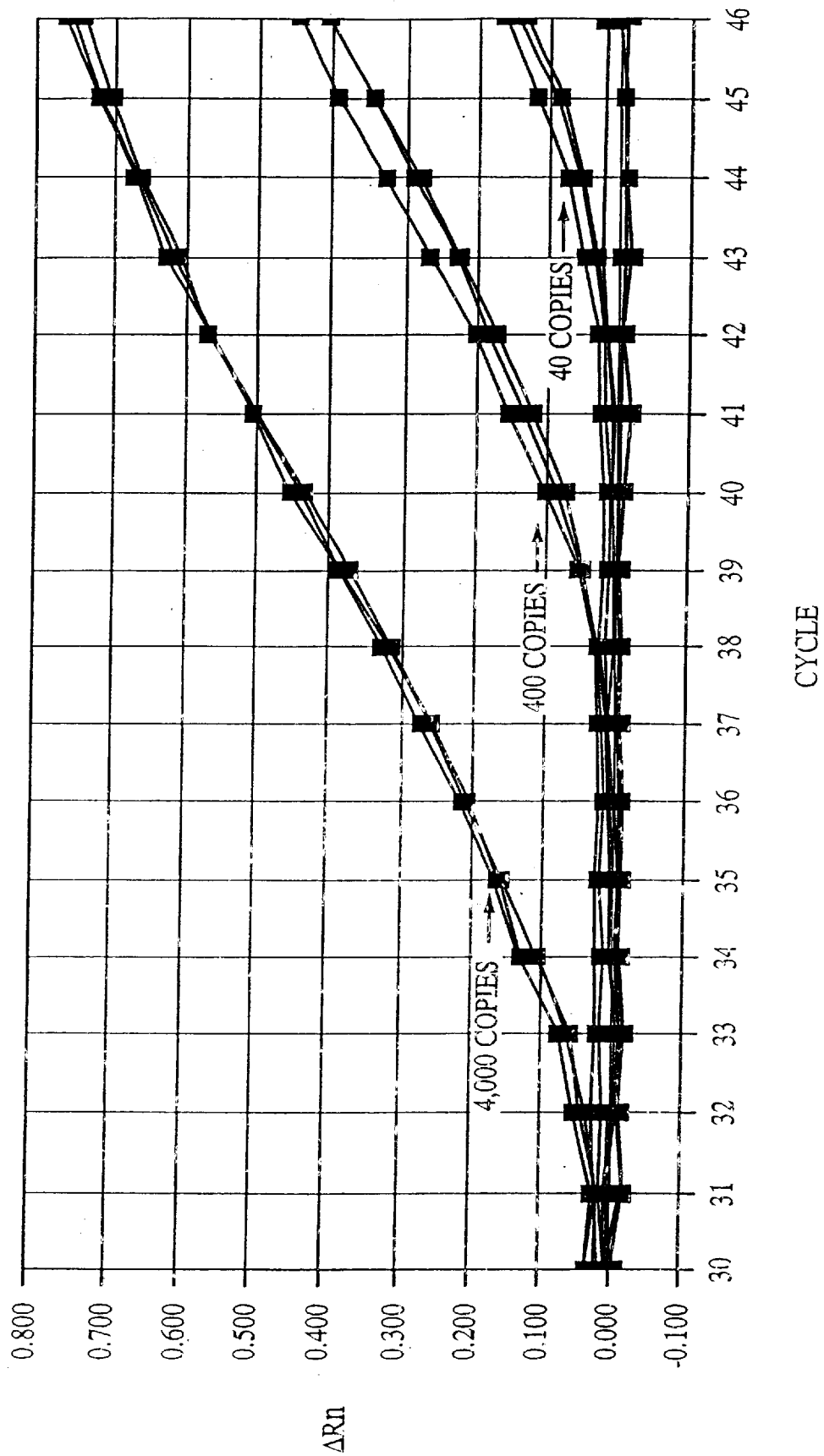

FIG. 7B is a graph depicting the detection and quantitation of *C. parvum* oocysts in a sample by QSD using the preferred primer pair and probe (i.e., [SEQ ID NO:2], [SEQ ID NO:3], and [SEQ ID NO:4], respectively).

Figure 7C:
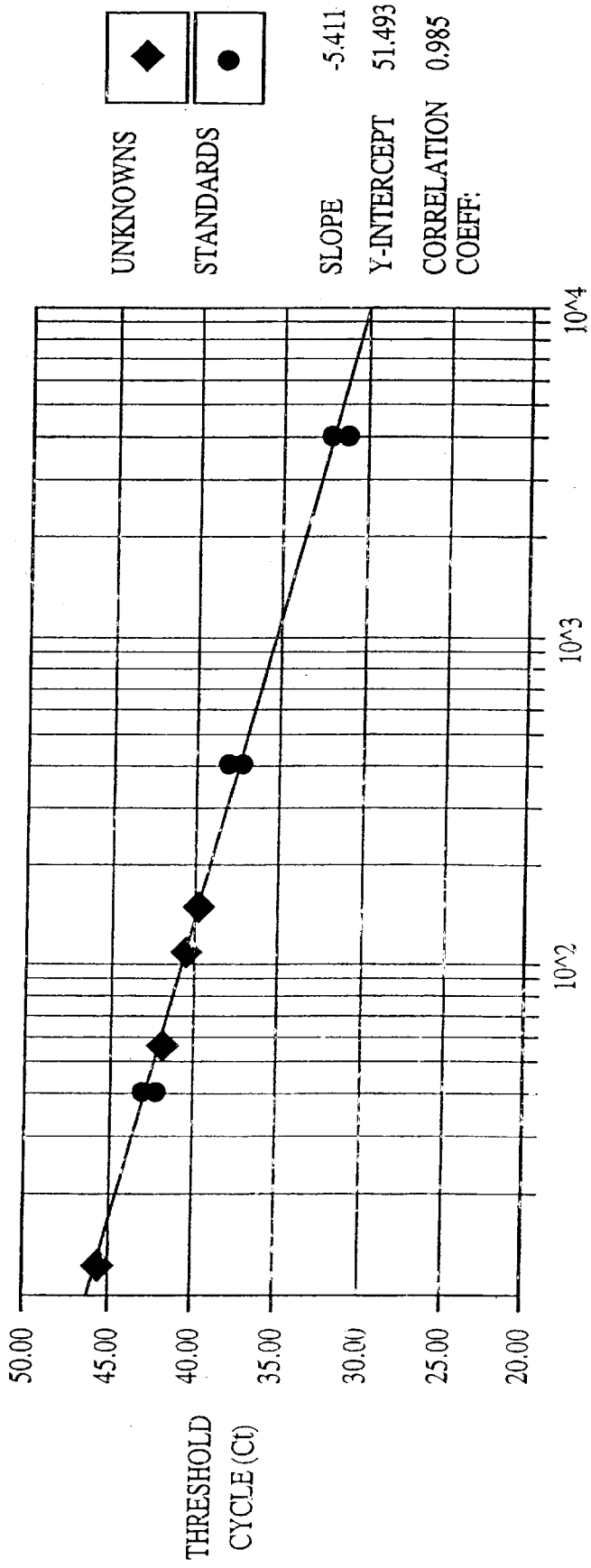

FIG. 7C is a graph depicting a standard curve demonstrating the relationship between sample fluorescence detected by QSD and the number of oocysts in the sample further demonstrating the quantitative ability of QSD to enumerate oocysts in unknown samples.

DETAILED DESCRIPTION OF THE INVENTION

The field of the invention is detection of *Cryptosporidium parvum* in aqueous samples. The invention includes a method for concentrating and detecting *Cryptosporidium parvum* organisms in a variety of water sample matrices, including but not limited to, environmental raw water samples, backwash water samples, process water samples, and finished water sample, preferably using an immunomagnetic separation (IMS) step. In one preferred embodiment, the method involves dissociating *C. parvum* oocysts from immunomagnetic microbeads coated with anti-Cryptosporidium antibodies while retaining oocyst viability. The dissociation procedure significantly removes bacterial contaminants from the sample such that it can be inoculated directly onto a susceptible cell culture and the cells can incubated to detect infectious *C. parvum* organisms in the sample. Moreover, the IMS step of the present invention triggers oocyst excystation which further simplifies the integrated cell culture procedure to detect infectious *C. parvum*.

The instant invention also includes novel PCR-based homogeneous (i.e., single-tube) format assays which do not require size determination of the PCR amplification product to confirm the specific amplification of the C. parvum target nucleic acid sequence. Therefore, the invention includes simple, one-tube, homogeneous format assays which obviate the need for complex recombinant DNA techniques to confirm that the amplification product is, indeed, of C. parvum origin based on a determination of the size of the PCR product. The methods of the invention are, therefore, less prone to operator error, faster, and may be fully automated.

More importantly, unlike standard PCR as described above, the PCR-based quantitative sequence detection (QSD) steps which may be used in the invention are quantitative and provide an estimate of the number of C. parvum organisms in the test sample. Further, in one embodiment of the invention, the method includes the combination of IMS with integrated cell culture and QSD to provide a quantitative assay which measures the number of infectious oocysts in a sample and may be used to detect oocysts in environmental raw water samples.

The method includes the step of concentrating C. parvum oocysts from various water sample matrices using immunomagnetic separation (IMS). Immunomagnetic separation, as used herein, refers to a method in which intact Cryptosporidium oocysts are bound by antibodies specific to Cryptosporidium, and the antibodies are, in turn, attached to a superparamagnetic microbead. The binding of the organisms to the beads allows for the separation of the parasites from an aqueous sample by the use of a magnet that attracts the beads and separates them from the aqueous phase. The beads are then washed and the organisms are recovered from the beads.

In one preferred embodiment, the immunomagnetic beads are coated with anti-Cryptosporidium antibodies which do not differentiate among the several species of this parasite. However, the invention should not be construed as being limited to these antibodies or to antibodies at all. Rather, the invention encompasses the use of magnetic microbeads coated with receptor molecules specific for a Cryptosporidium-specific ligand capable of binding the organism to the bead with sufficient affinity to allow washing of non-specifically bound molecules while retaining bound Cryptosporidium organisms. This receptor molecule includes, but is not limited to, polyclonal antibodies, monoclonal antibodies, lectins, and the like, which recognize Cryptosporidium-specific molecules on the surface of oocysts. It is preferred, however, that anti-Cryptosporidium antibodies be used.

Antibody is intended to refer to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, Fv, Fab and $F(ab)_2$, as well as single chains (e.g., Houston et al., 1988, Proc. Natl. Acad. Sci. USA 85:5879–5883; Bird et al., 1988, Science 242:423–426). An antibody or other receptor molecule which specifically recognizes and binds a molecule on the surface of intact *C. parvum* oocysts, but does not substantially recognize or bind to other molecules in an aqueous sample, e.g., a concentrated water sample, which contains *C. parvum* oocysts.

A significant feature of the IMS method described herein for concentrating *C. parvum* from a water sample is that the dissociation step which releases the oocysts from the immunomagnetic beads retains the viability and ability to infect susceptible cells of the oocysts. The immunomagnetic separation steps which may be used in the invention differ from the standard method in that the oocysts are dissociated from the immunomagnetic microbeads using an acidified Hank's buffered saline solution, pH 2.0–2.5, containing 1% trypsin (AHBSS/T) instead of the standard 0.1 N HCl. Dissociating the oocysts using AHBSS/T instead of HCl treatment offers several important improvements over prior art methods in that it preserves oocyst viability, triggers oocyst excystation and substantially rids the samples of bacterial contaminants. Thus, the modified IMS yields decontaminated samples containing concentrated, excystation-triggered *C. parvum* organisms which may be directly inoculated onto a susceptible tissue culture to detect viable, infectious organisms.

In one preferred embodiment, the oocysts are dissociated from immunomagnetic microbeads by incubating the beads in an acidified Hank's buffered saline solution, having a pH of from about 2.0 to about 2.5 and containing approximately 1% trypsin (AHBSS/T). Without wishing to be bound by theory, it is believed that trypsin may cleave the antibody molecules on the microbeads thereby releasing the bound oocysts. In any event, the invention should not be construed to be limited to dissociation of the oocysts from the microbeads using this particular buffer solution or to be limited solely to the use of trypsin. Rather, other low-pH buffer solutions of a pH from about pH 1 to about pH 4 may be used to dissociate the oocysts from the beads and to wash the beads thereby removing any matter non-specifically attached to the beads. Further, and alternatively, other proteases may be used to enzymatically release the oocysts from the microbeads while retaining oocyst ability to infect susceptible cells.

The method of the invention, by using IMS as a preferred concentration step, has the afore-mentioned advantages of reducing the bacterial contamination of the sample as well as triggering the oocysts to excyst upon inoculation onto a susceptible cell culture. However, the present invention should not be construed as being limited to these methods of sample decontamination or triggering excystation. Rather, the invention includes other methods of sample decontamination such as, for example, treatment with chlorine bleach followed by washing with a sterile solution containing sodium thiosulfate to remove residual chlorine as described in the '368 patent.

The present invention should not be construed to be limited solely to the excystation procedure using the AHBSS/T buffer. The invention encompasses other oocyst pre-treatment methods which cause excystation upon inoculation of the oocysts onto susceptible cells such as the pre-treatments described, for example, in the '368 patent, including, for example, incubating the oocysts in a cold solution containing chlorine bleach and then washing to remove the residual chlorine; and incubating the chlorine-decontaminated oocysts in an excystation solution consisting of 0.25% trypsin and 0.75% taurocholic acid to obtain excysted sporozoites. Recovered sporozoites may then be used to inoculate susceptible cells. Thus, conditions which enable decontamination of a sample potentially containing *C. parvum* oocysts and for the excystation of recovered oocysts are well known in the art of detection of *C. parvum* in aqueous samples and are encompassed in the present invention.

The present invention enables the detection of *C. parvum* in a variety of water samples matrices including, but not limited to, finished water, backwash water, process water, and environmental raw samples. Finished water generally refers to water which is ready for human consumption, i.e., water which is potable. Backwash water generally refers to water used to wash a filter, typically containing solids entrapped by the filter. Process water generally refers to water treated by any procedure which is the process of becoming potable. Environmental raw water sample, as used herein, is intended to refer to water from lakes, streams, creeks, rivers, reservoirs, wells, and all untreated water.

The aqueous sample used in the method of the invention preferably includes at least about 50% water which may potentially contain at least one C. parvum organism. The sample may be obtained from a naturally occurring water source or it may be prepared by adding water to a solid sample such as, for example, fecal matter or ground soil.

In one preferred embodiment, environmental raw water samples were centrifuged to produce a concentrate which was then assayed by IMS. However, other methods known in the art or to be developed may be used to concentrate environmental raw water samples including, but not limited to, calcium carbonate flocculation and filtration followed by dissolving the filters in acetone, and similar methods. It should be noted, however, that, unlike centrifugation, procedures involving calcium carbonate or acetone have a negative impact upon oocyst viability and are not preferred when detecting infectious oocysts.

Methods are also well known for differentiating between recovered oocysts which are intact but which are non-infectious and those which are infectious. In one preferred embodiment, infectious C. parvum organisms are detected by inoculating a sample following IMS onto susceptible cells and detecting the production of C. parvum-specific DNA encoding heat shock protein 70 (HSP70) in cultured cell lysates using PCR-based methods. However, additional methods known in the art or to be developed may also be used with the IMS step of the invention to determine if the C. parvum organism detected is infectious such as, for example, the inoculation of animals with sample concentrates, and the like. Accordingly, although the present invention includes steps to preferably detect genomic DNA encoding HSP70 in cell cultures inoculated with a test sample, other similar procedures which identify infectious oocysts are encompassed in the present invention.

In one preferred embodiment, following IMS, samples potentially containing C. parvum oocysts are inoculated onto confluent cultures of human ileocecal adenocarcinoma cells (HCT-8, obtained from the American Type Tissue Collection (ATCC), Rockville, Md.) which are susceptible to infection by C. parvum in that the cell cultures produce C. parvum nucleic acid, both DNA and RNA, within the infected cells within about 72 hours after addition of the C. parvum oocysts to the cells.

The cell culture inoculated is preferably 100% confluent HCT-8 cells. However, the invention should not be construed to be limited to these particular cells or to the particular inoculation or incubation conditions described. Rather, there are numerous cell lines, including but not limited to CaCo-2 cells and MDBK cells (both available from the ATCC), which are known in the art to be susceptible to infection by C. parvum and which produce C. parvum nucleic acids. Although other cells and conditions may be used to produce C. parvum nucleic acids in tissue culture, in the present method, cells are used which attach to the culture dish substratum, and the incubation period ranges from about 4 hours to about 72 hours. Such conditions are believed to minimize the detection of C. parvum nucleic acid from non-infectious oocysts which remain attached to the cells without being infectious. Otherwise, the literature is replete with references describing potentially susceptible cell lines which may be used to detect C. parvum in the method of the invention.

A PCR assay using genomic C. parvum DNA encoding the HSP70 protein is used as the amplification target to detect C. parvum DNA in a sample. However, the invention should not be construed as being limited to using DNA as a starting point for replication or even to being limited to the particular portion of the C. parvum genome disclosed. Regardless of the starting point, it is preferred that the target nucleic acid being amplified is unique to C. parvum and not be present in other species of Cryptosporidium or in other organisms.

The nucleic acid sequence should be sufficiently unique to C. parvum such that the identical sequence, or a sequence more than 60% homologous to it, does not occur in the mammalian cells used for cell culture, in other Cryptosporidium species, or in other organisms present in the aqueous sample being tested. By using a sufficiently unique nucleic acid target sequence, any PCR amplification product produced during the amplification phase will not complementary to and, therefore, will not cross-hybridize and/or amplify the nucleic acids of other organisms under high stringency conditions. Complementary refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

Homologous refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology.

A first oligonucleotide anneals with a second oligonucleotide with high stringency if the two oligonucleotides anneal under conditions whereby only oligonucleotides which are at least about 70%, and preferably at least about 90% or, more preferably, at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, *Molecular Cloning: A Laboratory Manual*, Cold Spring Harbor Laboratory, New York).

PCR is the preferred amplification technique used in the amplification step of the present methods. However, the amplification step may also be carried out using any suitable amplification technique known in the art or to be developed. Suitable amplification techniques are described in the following patents, each of which is incorporated herein by reference as if set forth in its entirety: U.S. Pat. Nos. 4,683,195; 4,683,202; 4,965,188; 5,409,818; 5,437,990; 4,957,858; and PCT Patent Publication No. 89/06995.

As described in the '368 patent, in the preferred PCR amplification procedure used in the present method, a target nucleic acid unique to the C. parvum organism is amplified by treating the double-stranded target polynucleotide with two oligonucleotide primers, each being complementary to one of the two strands of the target. The primers hybridize with their complementary strands and extension products are synthesized using DNA polymerase and at least four deoxyribonucleotide triphosphates (dNTPs). The extension products are separated from their complementary strands by denaturation at an elevated temperature, typically ranging from about 80° C. to about 100° C. The reaction mixture is repeatedly cycled between a low temperature annealing step usually ranging from about 37° C. to about 70° C. during which the primers hybridize to their complementary strands, an intermediate temperature (from about 70° C. to about 80° C.) primer extension step, to the higher temperature denaturation step at a temperature from about 80° C. to about 100° C. These temperature steps, or thermal cycling, are repeated many times, typically about 20 to about 40 cycles are carried out, followed by a final synthesis step at about 70° C. and a 4° C. soak to stop the reaction.

PCR reagents are the chemicals, apart from the target nucleic acid sequence, needed to perform the PCR process. As disclosed by Mayrand (1997, U.S. Pat. No. 5,691,146, which is incorporated by reference herein as if set forth in its entirety), these chemicals generally consist of five classes of components: (i) an aqueous buffer, (ii) a water soluble magnesium salt, (iii) at least four deoxyribonucleotide triphosphates (dNTPs) (conventionally, dATP, dTTP, dGTP, dCTP), (iv) oligonucleotide primers (typically two primers for each target sequence, the sequences defining the 5' ends of the two complementary strands of the double-stranded target sequence), and (v) a polynucleotide polymerase, preferably a DNA polymerase, more preferably a thermostable DNA polymerase, ie., a DNA polymerase which can tolerate temperatures between 90° C. and 100° C. for a total time of at least 10 minutes without losing more than about half its activity.

Primers for the amplification steps are the same if used for a reverse transcription step at the outset to convert RNA into DNA before carrying out the amplification procedure. Preferably, primers are chosen which only amplify target nucleic acid sequences from a single protozoan species within the genus Cryptosporidium. In the present invention, the primers amplify only a target nucleic acid sequence within C. parvum, because they have less than 60% sequence similarity to mammalian hsp70 genes. Therefore, amplification using the preferred primers does not amplify the mammalian homologs of Cryptosporidium hsp70 genes such that DNA extracted from mammalian cells following PCR in the absence of C. parvum template DNA will not yield the C. parvum-specific amplification product specified by these primers.

Preferred primer pairs and probes target the hsp70 gene sequence of C. parvum [SEQ ID NO:1] as disclosed by Khramtsov et al. (1995, J. Euk. Microbiol. 42:416–422) are shown in FIG. 1. A preferred primer pair ([SEQ ID NO:2] and [SEQ ID NO:3]) is used for standard PCR and for QSD. Another preferred primer pair is that disclosed in the '368 patent ([SEQ ID NO:5]and [SEQ ID NO:6]) which is also used for PCR and QSD. Each primer set has an internal oligonucleotide probe, ie., [SEQ ID NO:4] and [SEQ ID NO:7], which can be used to confirm the identity of the amplification product by PCR and/or QSD.

It will be understood by those skilled in the art based on this disclosure that other target DNA sequences specific for C. parvum other than the hsp70 gene DNA may be used to specifically identify C. parvum oocysts in an aqueous sample using PCR-based methods such as, for example, multiplex PCR using 18S rRNA as target nucleic acid sequences, and other similar methods. However, in the present invention, the target nucleic acid and the portion of the amplified target sequence to which the PCR oligonucleotide probe hybridizes are unique to C. parvum such that the probe and primers do not hybridize to nucleic acids of other organisms under conditions of high stringency. Thus, the nucleic acid-based detection method of the present invention only detects amplification of the specific, unique C. parvum target nucleic acid sequence and not that of other organisms which may be present in the sample.

In the standard PCR assay, the amplified target nucleic acid sequence can be detected directly by any method that can distinguish among the different lengths of DNA. Electrophoresis through agarose gels is the standard method known in the art for use in separating, identifying, and purifying DNA fragments following PCR. The location of the DNA within the gel can be determined directly by staining the gel with low concentrations of the intercalating fluorescent dye, ethidium bromide (EtBr). Band(s) corresponding to the predicted length for the amplified target DNA can then be detected by direct examination of the gel in ultraviolet light.

Additionally, the DNA bands from an electrophoresed sample can be probed by Southern blotting using a single-stranded oligonucleotide probe which is complementary to a sequence located between the two selected oligonucleotide primers in the amplified target nucleic acid sequence. Usually, the oligonucleotide probe is labeled with a radioactive or fluorescent tag, or attached directly or indirectly to an enzyme molecule such that the probe specifically bound to the immobilized complementary target sequence may be localized.

In the preferred embodiment herein, the oligonucleotide probe was complementary to the hsp70 sequence of C. parvum. However, the present invention is not limited to this sequence or to this gene. Rather, the oligonucleotide probe may be selected to hybridize to any target amplified nucleic acid located between two primer pairs all of which hybridize to a sequence in C. parvum but which do not hybridize to the nucleic acid of any other Cryptosporidium, mammal, or any other organism typically present in the aqueous samples of interest.

The oligonucleotides used in the invention may be synthesized by any standard method known or to be developed. Suitable syntheses are described in Ozaki et al. (1992, Nucleic Acids Res. 20:5205–5214) and Agrawal et al. (1990, Nucleic Acids Res. 18:5419–5423).

The oligonucleotide probes of the invention are preferably conveniently synthesized on an automated DNA synthesizer such as a Perkin-Elmer (Foster City, Calif.) Model 392 or 394 DNA/RNA synthesizer using standard chemistries, such as phosphoramidite chemistry described in Beaucage and Iyer (1992, Tetrahedron 48:2223–2311), Molko et al. (U.S.

Pat. No. 4,980,460), Koster et al. (U.S. Pat. No. 4,725,677), Caruthers et al. (U.S. Pat. Nos. 4,415,732 and 4,458,066). However, other similar syntheses using chemistries and techniques may be used. Alternative chemistries resulting in non-natural backbone groups, such as phosphorothioate, phosphoramidate, and the like, may also be used provided the hybridization efficiencies of the resulting oligonucleotides are not adversely affected.

Preferably, the oligonucleotide probe is in the range of about 15 to about 150 nucleotides in length. The precise sequence and length of an oligonucleotide probe of the invention depends in part on the nature of the target nucleic acid sequence to which it hybridizes. The binding location and length may be varied to achieve appropriate annealing and melting properties for a particular embodiment by one skilled in the art in accordance with known techniques such as "Taqman"-type assays.

Oligonucleotides of the present invention include linear oligomers of natural or modified monomers or linkages, such as deoxyribonucleotides, ribonucleotides, and the like, which are capable of specifically binding to a target polynucleotide by way of a regular pattern of monomer-to-monomer interactions, such as Watson-Crick base pairing. Usually, monomers are linked by phosphodiester bonds or their analogs to form oligonucleotides ranging in size from a few monomeric units, e.g., 3–4, to several tens of monomeric units. Whenever an oligonucleotide is represented by a sequence of letters, such as "ATGCCTG," it will be understood that the nucleotides are in a 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphoranilidate, phosphoramidate, and similar compounds.

In another preferred embodiment, amplification of the target nucleic acid sequence is detected by measuring the fluorescence of the reaction mixture in the presence of the thermostable intercalating fluorescent dye SYBR green 1 (Qualicon, Wilmington, Del.). The fluorescence detects the formation of any double-stranded DNA and is an indication that the target sequence specified by the primer pair has been produced.

In a preferred embodiment, amplification of the *C. parvum*-specific target sequence specified by the primer pair is detected by QSD. Preferably, a Model 7700 Sequence Detector laser fluorometer/thermal cycler is used for the QSD procedure to detect the fluorescence of the PCR sample mixture before and after each round of amplification. Such a QSD procedure is described in Heid et al. (1996, Genome Res. 6:986–994).

In another important aspect of the oligonucleotide probes of the present invention, the probes used for QSD include fluorescer and quencher molecules attached to the oligonucleotide. As used herein, the terms "quenching" and "fluorescence energy transfer" refer to the process whereby when a fluorescer molecule and a quencher molecule are in close proximity, whenever the fluorescer molecule is excited by an energy source, a substantial portion of the energy of the excited state nonradiatively transfers to the quencher where it either dissipates nonradiatively or is emitted at a different emission wavelength than that of the fluorescer.

It is well known that the efficiency of quenching is a strong function of the proximity of the fluorescer and the quencher, i. e., as the two molecules get closer, the quenching efficiency increases. As quenching is strongly dependent on the physical proximity of the reporter molecule and quencher molecule, it has been assumed that the quencher and reporter molecules must be attached to the probe within a few nucleotides of one another, usually with a separation of about 6–16 nucleotides (e.g., Lee et al., 1993, Nucleic Acids Res. 21:3761–3766). Typically, this separation is achieved by attaching one member of a reporter-quencher pair to the 5' end of the probe and the other member to a base 6–16 nucleotides away.

Preferably, fluorescer molecules are fluorescent organic dyes derivatized for attachment to the terminal 3' carbon or terminal 5' carbon of the probe via a linking moiety. Preferably, quencher molecules are also organic dyes, which may or may not be fluorescent, depending on the embodiment of the invention. For example, in a preferred embodiment of the invention, the quencher molecule is fluorescent. Generally, whether the quencher molecule is fluorescent or simply releases the transferred energy from the fluorescer by non-radiative decay, the absorption band of the quencher should substantially overlap the fluorescent emission band of the fluorescer molecule. Non-fluorescent quencher molecules that absorb energy from excited fluorescer molecules, but which do not release the energy radiatively, are referred to herein as chromogenic molecules.

Selection of appropriate fluorescer-quencher pairs for particular probes may be undertaken in accordance with known techniques such as those of, for example, Clegg et al., 1993, Proc. Natl. Acad. Sci USA 90:2994–2998; Wu et al., 1994, Anal. Biochem. 218:1–13; Pesce et al., 1971, In: *Fluorescence Spectroscopy*, Marcel Dekker, New York; and White et al., 1970, In: *Fluorescence Analysis: A Practical Approach*, Marcel Dekker, New York. Fluorescent and chromogenic molecules and their relevant optical properties from which exemplary fluorescer-quencher pairs may be selected are listed and described in, e.g., Berlman, 1971, In: *Handbook of Fluorescence Spectra of Aromatic Molecules*, 2nd ed., Academic Press, New York. Examples of derivatizing fluorescer and quencher molecules for covalent attachment via common reactive groups that can be added to an oligonucleotide in the present invention may be found in, e.g., Haugland, 1992, In: *Handbook of Fluorescent Probes and Research Chemicals*, Molecular Probes, Eugene, Oregon; U.S. Pat. No. 3,996,345; and U.S. Pat. No. 4,351, 760).

Preferred fluorescer-quencher pairs are xanthene dyes, including fluoresceins, and rhodamine dyes. Many suitable forms of these compounds are available commercially with substituents on their phenyl moieties which can be used as the site for bonding or as the bonding functionality for attachment to an oligonucleotide. Another preferred group of fluorescent compounds are the naphthylamines, having an amino group in the alpha or beta position. Included among such naphthylamino compounds are 1-demethylaminonaphthyl-5 sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine acridine orange; N-(p-(2-benzoxazolyl) phenyl)maleimide; benzoxadiazoles, stilbenes, pyrenes, and the like.

Most preferably, fluorescer and quencher molecules are selected from fluorescein and rhodamine dyes. These dyes and appropriate linking methodologies for attachment to oligonucleotides are well known in the art, and are described in U.S. Pat. No. 4,351,760; Marshall, 1975, Histochemical J. 7: 299–303; U.S. Pat. No. 5,188,934; European Patent Application 87310256.0; and International Application No. PCT/US90/05565, each of which is incorporated by reference herein as if set forth in its entirety.

In another preferred embodiment, amplification of the target nucleic acid sequence is detected by measuring the fluorescence of the reaction mixture in the presence of the thermostable intercalating fluorescent dye SYBR green 1 (Qualicon, Wilmington, Del.). The fluorescence detects the formation of any double-stranded DNA and is an indication that the target sequence specified by the primer pair has been produced.

In a preferred embodiment, amplification of the *C. parvum*-specific target sequence specified by the primer pair is detected by QSD. Preferably, a Model 7700 Sequence Detector laser fluorometer/thermal cycler is used for the QSD procedure to detect the fluorescence of the PCR sample mixture before and after each round of amplification. Such a QSD procedure is described in Heid et al. (1996, Genome Res. 6:986–994).

There are many linking moieties and methodologies for attaching fluorescer or quencher molecules to the 5' or 3' termini of oligonucleotides well known in the art and described, for example, in Eckstein, 1991, In: *Oligonucleotides and Analogues: A Practical Approach*, IRL Press, Oxford.

Preferably, commercially available linking moieties are employed that can be attached to an oligonucleotide during synthesis. Suitable moieties are available from Clontech Laboratories (Palo Alto, Calif.).

Rhodamine and fluorescein dyes are also conveniently attached to the 5' hydroxyl of an oligonucleotide at the conclusion of solid phase synthesis by way of dyes derivatized with a phosphoramidite moiety as described in, for example, U.S. Pats. Nos. 5,231,191 and 4,997,928.

In a preferred embodiment, the oligonucleotide probe includes the fluorescer molecule 6-carboxyfluorescein at its 5' end and the quencher molecule 6-carboxytetramethylrhodamine attached to the 3' end of the oligonucleotide probe. The fluorescer and quencher molecules are attached to the oligonucleotide probe as described in Livak et al. (1995, Guidelines for Designing TaqMan™ Fluorogenic Probes for 5' Nuclease Assays, In: *Perkin Elmer Research News*, Applied Biosystems Division, Foster City, Calif.). However, it will be understood based on this disclosure that the invention is not limited to this particular fluorescer-quencher pair or to the particular linkages used to attach the molecules to the probe. Rather, as previously discussed herein, a wide variety of fluorescer-quencher molecules may be attached to the oligonucleotide by a variety of linkages. Further, the fluorescer-quencher pair need not be located on nucleotides which are immediately adjacent; instead, the quencher dye may be attached to any nucleotide on a probe and still quench the fluorescence emission of a reporter dye attached to the 5' end (see Livak et al., supra).

One skilled in art of producing "Taqman" type probes would appreciate that probes should be of sufficient length to assure good hybridization and specificity of binding. Further, if possible, the GC content of the fluorogenic probe should range from about 40% to about 60%. Also, as described in Livak et al., supra, both PCR primers and the fluorogenic probe must hybridize to the target template strands during the annealing step of the PCR amplification. Because the fluorogenic probe is not extended at the 3' end, the template-probe hybridization is not stabilized by the DNA polymerase extension step which does stabilize the primer-template hybridization by extending from the 3' end of the primer. Thus, the $T_m$ of the probe-template hybrid must be higher than the primer-template hybrid $T_m$.

Moreover, the $T_m$ of the probe should be higher than the annealing temperature used in the PCR.

In one preferred embodiment, the fluorescer molecule is released by the 5'→3' exonuclease activity of the Taq DNA polymerase during amplification thereby causing the separation of the fluorescer and quencher such that the fluorescence level of the sample is increased but leaving the fluorescence of the quencher molecule essentially unchanged such that it serves as an internal standard. However, the invention should not be construed to be limited to the release of a fluorescer from the oligonucleotide probe in order to cause fluorescence of a sample as the target DNA is amplified. Rather, one skilled in the art would recognize that the essential feature of the present invention is the differential quenching of the reporter fluorescer molecule as a result of synthesis of the target nucleic acid sequence. For example, as described in U.S. Pat. No. 5,691,146, QSD may be performed using oligonucleotide probes which, when present in the single-stranded state in solution, are configured such that the fluorescer and quencher are sufficiently close to substantially quench the reporter fluorescer's emission. However, upon hybridization of the intact quencher-fluorescer oligonucleotide probe with the amplified target nucleic acid sequence, the fluorescer and quencher molecules come to be sufficiently distant from each other. As a result, the quenching is substantially abated causing an increase in the fluorescence emission detected. The QSD of the present invention includes differential quenching of the reporter fluorescer molecule due to the interaction of the fluorescer-quencher probe with the amplified target nucleic acid sequence. The precise mechanism by which the quencher-fluorescer molecules are brought together or taken apart may vary. Guidelines for designing, producing, and using appropriate fluorescer-quencher oligonucleotide probes are known in the art and are described in the above-cited references including, for example, Livak et al. (1995, Guidelines for Designing TaqMan™ Fluorogenic Probes for 5' Nuclease Assays, In: *Perkin Elmer Research News*, Applied Biosystems Division, Foster City, Calif.).

The 3' terminal nucleotide of the oligonucleotide probe may be rendered incapable of extension by a nucleic acid polymerase in one embodiment of the invention. Such blocking may be carried out by the attachment of a fluorescer or quencher molecule to the terminal 3' carbon of the oligonucleotide probe by a linking moiety, or by making the 3'-terminal nucleotide a dideoxynucleotide. Alternatively, the 3' end of the oligonucleotide probe may be rendered impervious to the 3'→5' extension activity of a polymerase by incorporating one or more modified internucleotide linkages onto the 3' end of the oligonucleotide. Minimally, the 3' terminal internucleotide linkage must be modified, however, additional the internucleotide linkages may be modified. It is preferred that the 5'→3' exonuclease ability of the DNA polymerase to cleave off the 5' nucleotide to which the fluorescer molecule is attached is preserved.

Internucleotide modifications which prevent elongation from the 3' end of the oligonucleotide probe and/or which block the 3'→5' exonuclease activity of the DNA polymerase during PCR may include phosphorothioate linkages, methylphosphonate linkages, boranophosphate linkages, and other similar polymerase-resistant internucleotide linkages. An alternative method to block 3' extension of the probe is to form an adduct at the 3' end of the probe using mitomycin C or other like antitumor antibiotics such as those of Basu et al., 1993, Biochemistry 32:4708–4718). Thus, the precise mechanism by which the 3' end of the oligonucleotide probe is protected from cleavage is not essential so long as the quencher molecule is not cleaved from the oligonucleotide probe.

The level of fluorescence is preferably measured using a laser/fluorometer such as, for example, a ABI Prism Model 7700 Sequence Detector or a BAX™ fluorometer. However, similar detection systems for measuring the level of fluorescence in an aqueous sample are included in the invention.

Briefly, QSD is similar to standard PCR assays in that DNA is used as a DNA template to generate millions of copies of the target DNA by *Thermus aquaticus* (Taq) DNA polymerase enzyme and thermal cycling. However, QSD differs greatly from PCR in that QSD involves the detection of the hybridization of a nonextendible internal fluorogenic quencher-fluorescer DNA probe (e.g., a TaqMan™ probe, Perkin Elmer, Foster City, Calif.) which contains a fluorescer molecule at one end and a quencher molecule on the other end and which is specific for the target DNA sequence being amplified as described in Heid et al. (1996, Genome Res. 6:986–994). When the probe is intact, fluorescent energy transfer occurs and the reporter dye fluorescence is absorbed by the quenching dye (id. at 987). During the extension phase of the PCR cycle, the fluorescent hybridization probe is cleaved by the 5'→3' exonuclease activity of the DNA polymerase. Once the probe is cleaved, the reporter dye emission is no longer quenched resulting in an increase of the reporter dye fluorescence emission spectra after each round of replication.

Further, the model 7700 sequence detector measures the intensity of the quenching dye emission, which changes very little over the course of the PCR reaction, and uses this measure as an internal standard with which to normalize the reporter dye emission variations. Moreover, the software calculates the threshold cycle ($C_T$) which is the cycle number at which the change in normalized reporter signal ($\Delta R_n$) crosses a selected threshold point. The change in normalized reporter signal is also calculated by the software by measuring the emission intensity of the reporter divided by the emission of the quencher in a reaction tube and subtracting the same value obtained prior to PCR amplification in that same reaction tube. As demonstrated herein, the threshold cycle is a function of the starting quantity of target DNA and, thus, the point at which the amplification plot crosses the threshold is predictive of the quantity of input target. By determining the threshold cycle for reference standards having known amounts of *C. parvum* oocysts, a reference standard may be developed which enables the quantitation of oocysts in unknown samples. The data disclosed demonstrate that quantitative sequence detection either with or without integrated cell culture, provides a simple, efficient, closed-tube assay which is both sensitive and quantitative for *C. parvum* oocysts in water samples.

Accordingly, unlike ethidium bromide staining of gel fragments, QSD fluorescence is directly proportional to the amount of fluorescer-quencher probe bound to the specific target DNA in the sample. Thus, by proper data analysis included with the ABI Prism Model 7700 Sequence Detector (Perkin-Elmer Applied Biosystems, Foster-City, Calif.), the amount of amplified *C. parvum*-specific target DNA in the sample may be deduced based upon the level of fluorescence detected in the sample and used to generate a standard curve to quantitate the number of oocysts in any given sample.

In a preferred embodiment, the QSD procedure of the invention is used to detect *C. parvum* oocysts without either IMS or integrated cell culture prior to the amplification step of the QSD procedure. However, it will be understood based on this disclosure that the invention includes the use of these various procedures in combination with each other such that, for instance, IMS may be used with any nucleic acid amplification-based method, with or without being followed by integrated cell culture; alternatively, another concentration procedure may be used with the integrated cell culture of the present invention followed by QSD, or IMS may be followed directly by QSD without cell culture, or any other combination of the above-mentioned procedures may be performed in combination with QSD.

The invention also includes a kit for detecting *C. parvum* nucleic acid. The kit comprises a primer pair which amplifies a unique target sequence of the *C. parvum* genome. In a preferred embodiment, the target *C. parvum* nucleic acid is the hsp70 gene (SEQ ID NO:1) and the forward and reverse primers have the sequences SEQ ID NO:2 and SEQ ID NO:3, respectively. In another preferred embodiment, the oligonucleotide probe used to detect the amplification product has the sequence SEQ ID NO:4. However, the present invention is not limited to these primers or oligonucleotide probe sequences. Rather, any oligonucleotide probe having a sequence between the two primers spanning from nucleotide residue 1120 up to and including nucleotide residue 1465 is encompassed in the invention.

The kit is used pursuant to the methods disclosed in the invention. Briefly, the kit may be used with or without IMS concentration of oocysts and with or without the integrated cell culture procedures of the present invention. Further, the kit may be used in standard PCR, or in a homogeneous format PCR procedure as described herein. One skilled in the art would appreciate based on the disclosure herein that the kit may used in any of the afore-mentioned procedures and in any combination thereof.

The invention is further described in detail by reference to the following non-limiting examples provided for purposes of illustration only.

EXAMPLE 1
Detection of Oocysts by Standard PCR Procedure

The experiments presented in this example may be summarized as follows. Oocysts were detected in environmental water samples by first concentrating the samples using a modified IMS technique followed by either standard PCR alone or by standard PCR coupled with cell culture (CC-PCR). As stated previously herein, the modified immunomagnetic separation method differs from the standard method in that AHBSS/T is used to dissociate the oocysts from the immunomagnetic microbeads instead of the 0.1 N HCl. Dissociating the oocysts using AHBSS/T instead of HCl preserves oocyst viability, triggers oocyst excystation, and provides substantial decontamination of the samples. Thus, the modified IMS yields decontaminated samples containing concentrated, excystation-triggered *C. parvum* organisms which may be directly inoculated onto a susceptible tissue culture to detect viable, infectious organisms. The effectiveness of this method to detect *C. parvum* organisms was confirmed by standard immunofluorescence techniques and the sensitivity of the procedure was determined. The data disclosed demonstrate that the invention achieves the efficient, sensitive and selective detection of infectious *C. parvum* oocysts from environmental raw water samples.

The materials and methods used in this example are as follows.

Oocyst Stocks

Purified, live *C. parvum* oocysts were obtained from Waterborne, Inc. (New Orleans, La.). Oocyst stocks were counted by immunofluorescence assay (IFA) microscopy as described in by the U.S. Environmental Protection Agency ICR (1996, Fed. Regist. 61:24354–24388). *Cryptosporidium parvum* oocysts were also obtained from the University of Idaho as unpurified fecal samples from infected neonatal calves. Oocysts were purified by sucrose, Percoll-sucrose, or cesium chloride gradients, as described, for example, by LeChevallier et al. (1996, Proc. Amer. Water Works Assoc. Water Qual. Tech. Conf. in Boston, Mass., Amer. Water Works Assoc., Denver, Colo.) and Dubey et al. (1990, In: *Cryptosporidiosis of man and animals*, CRC Press, Boca Raton, Fla.).

Immunomagnetic Separation Recovery of Oocysts

Raw, backwash and seeded water grab samples (10 to 11 liters) were concentrated by centrifugation. Cryptosporidium oocysts were recovered from water concentrates using immunomagnetic microbeads coated with antibodies specific for Cryptosporidium oocysts (Dynabeads anti-Cryptosporidium, Dynal, Oslo, Norway). Water concentrates equivalent to a 0.5 ml packed pellet were added to Leighton tubes containing, Milli-Q water (Milli-Q filter system, Millipore, Bedford, Mass.) and the final volume was adjusted to 10 ml per tube using Mlilli-Q water. One milliliter of 10×SL buffer-A and 1 ml SL buffer-B, both provided with the microbeads, were added to each tube followed by adding 100 μl of microbeads. The Leighton tubes were placed on a Dynal rotary mixer and mixed at a rate of 23–25 rpm for about 1 to about 2 hours.

Microbead-oocyst complexes were recovered using the Dynal magnetic particle concentrator-1 (MPC-1) for 2 minutes. The supernatants were decanted with the MPC-1 magnet-side-up. The Leighton tubes were removed from the MPC-1 and the samples were resuspended in 1×SL buffer-A using a Pasteur pipet and the resuspended samples were transferred to microfuge tubes. The samples were resuspended by gentle inversion and were placed in the microfuge tube magnetic particle concentrator (MPC-M) without the magnetic strip. The magnetic strip was inserted into the MPC-M and the samples were concentrated for 2 minutes and the supernatants were aspirated from the tubes. The magnetic strip was removed and the samples were resuspended in 1 ml of 1× phosphate buffered saline (PBS) and then the samples were concentrated with the MPC-M as previously described herein. The magnetic strip was removed and 200 μl of acidified Hank's buffered salt solution, pH 2.0–2.5, containing 1% trypsin (AHBSS/T), were added to each sample if the sample was to be processed that day. If the sample was to be processed the next day, 180 μl of neutral HBSS (NHBSS) were added to each sample and the sample was vortexed and stored at 4° C. overnight until further processing. Samples processed in a single day were vortexed for 10 seconds and incubated at 37° C. for 1 hour as described below.

For samples processed over a period of two days, 20 μl of AHBSS/10% trypsin, pH 2.0, and 2 μl of 1M HCl were added to each tube which had been stored overnight at 4° C. and, identically to the samples processed all in one day, the samples were vortexed for 10 seconds and then incubated for 1 hour at 37° C. with vortexing every 15 minutes. As stated previously herein, this novel, multipurpose treatment serves to dissociate the oocysts from the microbeads while preserving viability, offers bacterial decontamination of the sample, and triggers oocysts excystation upon inoculation with susceptible cultured mammalian cell monolayers with the sample.

After incubation for 1 hour with vortexing, the samples were placed into the MPC-M without the magnetic strip, the magnetic strip was inserted, and the samples were allowed to stand for 10 seconds. The supernatants, containing recovered oocysts, were transferred to clean microfuge tubes. In order to increase the recovery of oocysts by this procedure, a second wash was performed to release any oocysts still bound to the microbeads by resuspending the microbeads in 100 μl of AHBSS/T, pH 2.0, vortexing the sample, and separating the microbeads from the wash as previously described. The two wash supernatants of each sample were pooled and each dissociated sample was neutralized by the addition of 4 μl of 0.5 N NaOH. The neutralized samples were centrifuged at 15,000 rpm in a microfuge for 2 minutes with no brake. The supernatants were aspirated leaving a volume of approximately 20 μl. The samples were resuspended by adding 180 μl of growth medium pre-warmed at 37° C. to each tube. The samples were used immediately to inoculate cell monolayers (100 μl of sample per tissue culture well).

Detection of Oocysts Seeded into Environmental Water Samples

*C. parvum* oocysts were seeded into raw environmental water samples and then recovered by IMS as described above. Briefly, known numbers of oocysts were seeded into raw water concentrates up to 0.1 ml in pellet volumes to determine the efficiency and detection limits of the procedure. The oocysts were recovered from the concentrates essentially as described above.

Cell Culture Infectivity Assay

To determine the infectivity of the IMS-recovered oocysts, recovered oocysts were inoculated onto in vitro cultured monolayers of susceptible mammalian cells. Human ileocecal adenocarcinoma (HCT-8) cells obtained from the American Type Tissue Collection (CCL-244, ATCC, Rockville, Md.), were cultured to 100% confluence in 96-well cell culture microtiter plates as described in Woods et al. (1995, FEMS Microbiol. Lett. 128:89–94). The cell culture maintenance medium consisted of Roswell Park Memorial Institute (RPMI) 1640 medium with L-glutamine supplemented with 5% fetal bovine serum (FBS), pH 7.2. The growth medium used for the in vitro development of *Cryptosporidium parvum* contained 10% FBS, 15 mM HEPES (N-[2-hydroxyethyl]piperazine-N'-[2-ethanesulfonic acid]), 50 mM glucose, 35 μg/ml ascorbic acid, 1 μg/ml folic acid, 4 μg/ml aminobenzoic acid, and 2 μg/ml calcium pantothenate as described by Upton et al. (1995, J. Clin. Microbiol. 33:371–375). Twenty-four hours prior to parasite inoculation, the 96-well plates were seeded with $8 \times 10^4$ HCT-8 cells per well. The plates were incubated at 37° C. in a 5% carbon dioxide and 95% air humidified incubator to allow for the development of 100% confluent monolayers.

For inoculation of cell monolayers, 50 μl of maintenance medium were removed from each well and 100 μl of freshly pretreated oocysts resuspended in growth medium pre-warmed to 37° C. (100 μl to 200 μl total volume) were added to each well. The inoculated cell monolayers were incubated at 37° C. in a 5% carbon dioxide and-95% air humidified incubator for 72 hours. Following incubation, the monolayers were washed five times with 200 μl volumes of phosphate buffered saline (PBS) to remove unexcysted, noninfectious oocysts. The cell monolayers were harvested by the addition of 1× Tris-EDTA buffer, pH 8.0 (TE), and the cells were resuspended and transferred to microfuge tubes. The harvested cells were centrifuged at 15,000 rpm in a microfuge for 2 minutes and the supernatants were aspirated leaving approximately 10 μl per tube. The samples were frozen at −20° C. until further analysis.

Preparation of DNA Extracts

Lysates were prepared from the cells as described by Di Giovanni et al. (1998, Proc. Amer. Water Works Assoc.

Water Qual. Tech. Conf. in San Diego, Calif., Amer. Water Works Assoc., Denver, Colo.). Briefly, DNA was released from the oocysts and HCT-8 cells by eight cycles of freezing in liquid nitrogen and thawing in a 98° C. heating block. Aliquots of lysed samples were used directly for PCR, homogeneous format assays, or QSD, without further purification.

DNA Primers and Probes

PCR primers were designed to specifically and efficiently amplify a region of the *Cryptosporidium parvum* hsp70 DNA [SEQ ID NO:1]. The primer pair was as follows: the forward primer sequence was 5' TCCTCTGCCGTACAG-GATCTCTTA 3'[SEQ ID NO:2], and the reverse primer sequence was 5' TGCTGCTCTTACCAGTACTCTTATCA 3'[SEQ ID NO:3]. This primer pair combination results in a 346 basepair amplification product from *C. parvum* hsp70 DNA [SEQ ID NO:1]. An internal oligonucleotide probe was then used to confirm the identity of the amplification product. The internal probe sequence was as follows: 5'TGT-TGCTCCATTATCACTCGGTTTAGA 3'[SEQ ID NO:4].

Alternatively, the probe and primer pair described by De Leon and Rochelle (1998, U.S. Pat. No. 7,770,368) were used. This primer pair combination results in a 361 basepair amplification product from *C. parvum* hsp70 DNA [SEQ ID NO:1]. The primer pair was as follows: the forward primer sequence was 5' AAATGGTGAGCAATCCTCTG 3'[SEQ ID NO:5], and the reverse primer sequence was 5'CTTGCT-GCTCTTACCAGTAC 3'[SEQ ID NO:6]. An internal oligonucleotide probe was then used to confirm the identity of the amplification product. The internal probe sequence was as follows: 5' CCAT-TATCACTCGGTTTAGA 3'[SEQ ID NO:7].

Polymerase Chain Reaction

To detect intact oocysts, DNA obtained from lysates of IMS recovered oocysts was used directly in standard PCR. For the detection of viable, infectious oocysts, DNA obtained from HCT-8 cell harvests was used in CC-PCR. In either case, the PCR primer pair, SEQ ID NO:2 and SEQ ID NO:3, specific for the *C. parvum* hsp70 gene was used. This primer set yields a 346 basepair PCR product from *C. parvum* DNA. Each 50 µl PCR mixture contained 5 µl of 10× amplification buffer with Mg (Boehringer Mannheim, Indianapolis, Ind.); 1 µl of a 10 mM mix of dATP, dTTP, dCTP, and dGTP (10 mM each, Boehringer Mannheim, Indianapolis, Ind.); 10.0 pmol each of the forward [SEQ ID NO:2] and reverse [SEQ ID NO:3] primer; and 2.5 µl of 30 mg/ml bovine serum albumin (BSA, Sigma Chemical Co., St. Louis, Mo.).

The reaction mixtures were overlaid with sterile mineral oil and the PCR was performed using a Perkin-Elmer model 480 or model 9600 DNA thermal cycler (Perkin-Elmer, Foster City, Calif.). The amplification conditions were as follows: the initial denaturation was performed at 95° C. for 5 minutes, the samples were held at 80° C. while 2.0 U of Taq DNA polymerase (Boehringer Mannheim, Indianapolis, Ind.) were added "hot start," and 40 cycles of denaturation at 94° C. for 30 seconds, annealing for 1 minute at 60° C., and extension at 72° C. for 30 seconds were carried out followed by a single final extension at 72° C. for 10 minutes and a 4° C. soak to stop the reaction.

Alternatively, the primer pair [SEQ ID NO:5] and [SEQ ID NO:6] was used pursuant to the '368 patent. For this primer pair, the thermal cycling program was as described previously except the annealing temperature was either 55° C. or 59° C. as set forth in the description of the figures.

Detection of PCR Amplification Product

Detection of PCR amplification product was essentially as previously described elsewhere herein. Briefly, the amplification products were separated by horizontal gel electrophoresis on a 2.0% agarose gel (Amresco, Solon, Ohio) containing 0.5 µg/ml EtBr (Sigma Chem. Co., St. Louis, Mo.) and the separated fragments were visualized under UV light. Photographic gel images were captured using a gel documentation system (UVP, Inc., Upland, Calif.).

Additionally, the PCR products were cloned using a TOPO TA cloning kit (Invitrogen, Carlsbad, Calif.) per the manufacturer's instructions, and the cloned products were sequenced by a commercial laboratory (ACGT, Northbrook, Ill.). Thus, the sequence homology of the cloned amplification product insert to the *C. parvum* hsp70 gene (GenBank Acc. No. U11761) was confirmed. Standard molecular biology techniques were performed pursuant to standard methods described in the '368 patent.

The Results of the experiments are as follows.

Field Test of IMS/PCR Oocyst Detection Method

IMS of naturally occurring *C. parvum* oocysts from environmental water samples followed by infectivity determination using integrated CC-PCR was field tested to determine the efficacy of the technique.

Over 100 each raw water source and filter backwash water grab samples from twenty-five sites throughout the United States were analyzed. Oocyst seeded raw and filter backwash water samples were also used to evaluate recovery efficiencies and compare the performance of the CC-PCR among different water quality matrices.

The grab samples were concentrated by centrifugation, the concentrates were split and purified by IMS. An acidified Hank's balanced salt solution containing 1% trypsin (AHBSS/T) was used to dissociate any captured oocysts from the IMS beads since the manufacturer-recommended 0.1 N HCl dissociation buffer affected oocyst viability. IMS-purified samples were used to directly inoculate susceptible cell (i.e. human ileocecal HCT-8 cells) monolayers grown in 96-well microtiter plates. Using *C. parvum*-specific PCR primers ([SEQ ID NO:5] and {SEQ ID NO:6]), infectious *Cryptosporidium parvum* was detected in 6 raw and 9 filter backwash water samples. All CC-PCR positive samples were confirmed by cloning and DNA sequence analysis of the PCR amplification products.

Additionally, environmental raw water concentrates were seeded with known numbers of oocysts to determine the sensitivity limits of the combined IMS/PCR procedure with or without integrated cell culture. The results were compared to ELISA assays for infectious oocysts.

Comparison of IMS Oocyst Recoveries and CC-PCR of Seeded Water Samples

IMS recoveries of *C. parvum* oocysts from seeded raw and backwash samples were determined by immunofluorescence assay (IFA) microscopy as described in U.S. Environmental Protection Agency ICR (1996, Fed. Regist. 61:24354–24388), and the results are summarized in Table 1. The results of CC-PCR for each sample are also included in Table 1 for comparison with the IFA results.

TABLE 1

| Sample | IMS Count | % | CC-PCR |
|---|---|---|---|
| Raw1 | 408 | 56.6 | POS |
| Raw2 | 136 | 33.7 | POS |
| Raw3 | 42 | 10.4 | POS |
| Raw4 | 28 | 6.9 | POS |
| Raw5 | 112 | 27.8 | ND* |
| Raw6 | 86 | 21.0 | POS |

TABLE 1-continued

| Sample | IMS Count | % | CC-PCR |
|---|---|---|---|
| Mean recovery, raw water | 26.1 ± 16.5% | | 100% agreement between IFA and CC-PCR |
| Backwash1 | 124 | 17.2 | POS |
| Backwash2 | 0 | <1.7 | NEG |
| Backwash3 | 3 | 6.2 | POS |
| Backwash4 | 29 | 7.2 | ND* |
| Backwash5 | 16 | 18.2 | POS |
| Backwash6 | 0 | <3.4 | NEG |
| Mean recovery, backwash water | 9.0 ± 6.4% | | 100% agreement between IFA and CC-PCR |

*Not Determined, invalid CC-PCR assays due to a power failure during PCR and an incubator malfunction, respectively.

The IMS recoveries were lower than those previously disclosed in the prior art (see, e.g., Woods et al., 1995, FEMS Microbiol. Lett. 128:89–94; Bukhari et al., 1997, Abstract, Proceedings of the Water Quality Technology Conference, American Water Works Association, Denver, CO; Campbell et al., 1997, In: *International Symposium on Waterborne Cryptosporidium*, Fricker et al., eds., American Water Works Association, Newport Beach, Calif.). Without wishing to be bound by theory, these differences may be due to the fact that prior art methods involve 10 ml samples seeded directly with *C. parvum* oocysts which did not include loss of oocysts during concentration and sample handling. The prior art studies also involve dissociation of oocysts from the beads using the much harsher 0.1 N HCl dissociation method followed by microscopic enumeration. On the other hand, the method disclosed herein entails dissociation by AHBSS coupled with trypsin digestion which retains oocyst viability making the claimed method compatible with an integrated cell culture assay for viable, infectious organisms.

Data disclosed herein demonstrate that when a 10 ml reverse osmosis water sample is seeded directly with oocysts, a mean recovery of 92.6% (n=3) is obtained using the 0.1 N HCl dissociation method compared with a mean recovery of 61.2% (n=6) using the AHBSS/trypsin dissociation method. Therefore, although the AHBSS/T dissociation method decreases oocyst recovery, the method offers several advantages over the 0.1 N HCl dissociation method which is not compatible with an integrated cell culture assay in that dissociation of oocysts using AHBSS/T preserves the ability of the oocysts to infect susceptible cells, substantially decontaminates the sample, and provides an excystation trigger for the parasite.

CC-PCR results agree with all IFA oocyst counts with the exception of two invalid CC-PCR assays as noted in Table 1. This includes the positive CC-PCR assay for the seeded Backwash3 sample which had an IFA count of only 3 oocysts. In addition, 8 reverse osmosis water sample negative controls were all found to be negative by IFA and CC-PCR. These results support the high sensitivity of the claimed CC-PCR assay and its successful application, for the first time, to the analysis of environmental water samples including samples of low water quality as disclosed below.

Detection of Infectious *Cryptosporidium parvum* in Environmental Water Samples by CC-PCR Over 100 each raw source and filter backwash grab samples from twenty-five sites in the United States were analyzed. Of the samples assayed, 6 raw environmental samples and 9 filter backwash water samples tested positive for infectious *C. parvum* by CC-PCR. All PCR amplification products were confirmed by cloning and sequence analysis to be >98% homologous to the *C. parvum* hsp70 gene used as a DNA target.

Therefore, the disclosed *Cryptosporidium parvum* infectivity assay integrates in vitro cell culture of the parasite with PCR detection (CC-PCR) preceded by a modified IMS separation step. The data disclosed herein demonstrate that IMS recovery followed by integrated cell culture and PCR detection offers several advantages over prior art methods including the recovery of viable oocysts without bacterial contamination where the oocysts are triggered to excyst upon inoculation onto permissive cell monolayers. Thus, the disclosed method obviates the requirement of a heat shock step followed by reverse-transcriptase and is therefore less time-consuming than RT-PCR. More importantly, IMS purification allows the detection of oocysts from raw environmental samples not possible using prior art methods, as well as from filter backwash water, process water, finished water samples, and the like.

PCR Detection of Total Oocysts

Figure 2:
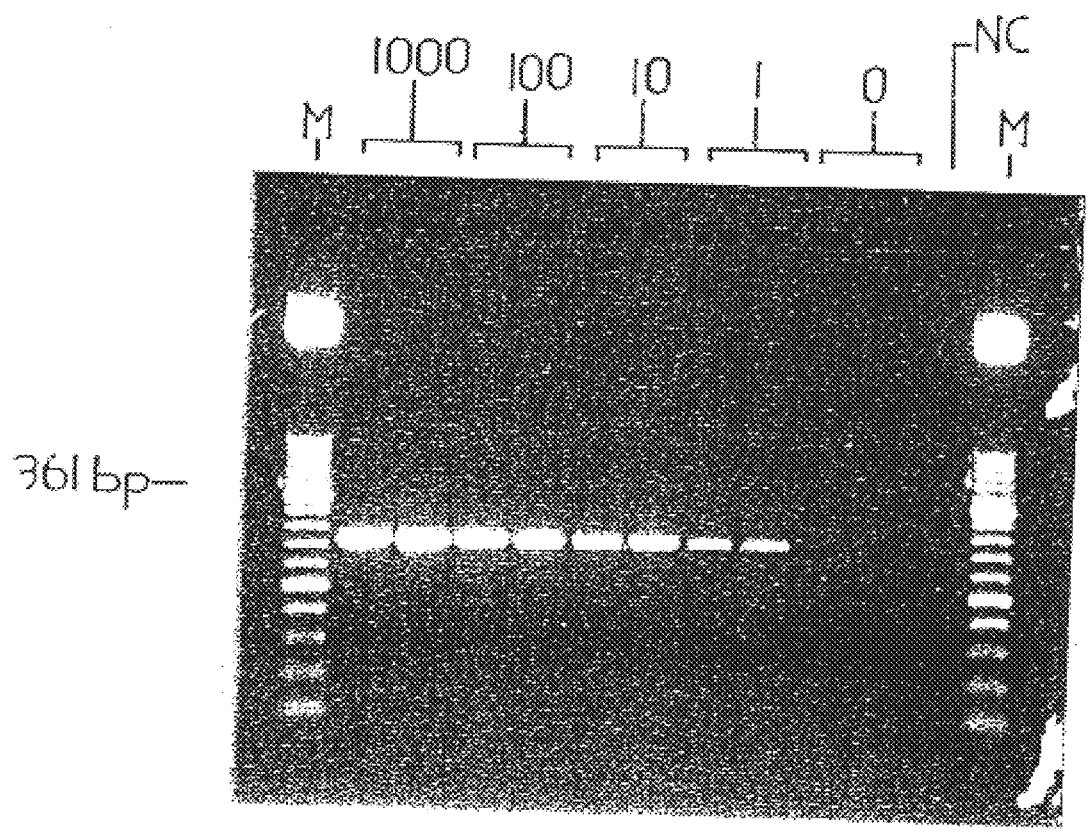
FIG. 2 is an image of a DNA gel depicting the detection limit of standard PCR performed at an annealing temperature of 55° C.

Standard PCR using the primer pairs and probe described by De Leon and Rochelle (U.S. Pat. No. 5,770,368) which are specific for the hsp70 gene of *C. parvum* revealed a detection limit of 1 to 2 oocysts, based on ten-fold dilutions of an oocyst stock titered using a hemocytometer (FIG. 2). FIG. 2 demonstrates the visualization of the 361 predicted size amplification product by ethidium bromide stained agarose gel electrophoresis. The data disclosed demonstrate a detection limit of approximately 1–2 oocysts using a PCR annealing temperature of 55° C. and the absence of background in the negative control (NC, no template DNA) sample. For reference, a 2,000 to 50 bp molecular weight marker lane (M) is included in the outermost lanes on either side of the gel.

Detection of Infectious Oocysts by Cell Culture-PCR

Oocysts recovered by IMS from seeded raw water concentrates were divided equally for standard PCR and for cell culture-PCR analyses. Oocysts recovered from environmental samples by IMS were suitable for PCR analyses and for inoculation of HCT-8 cells without further purification.

Figure 3:
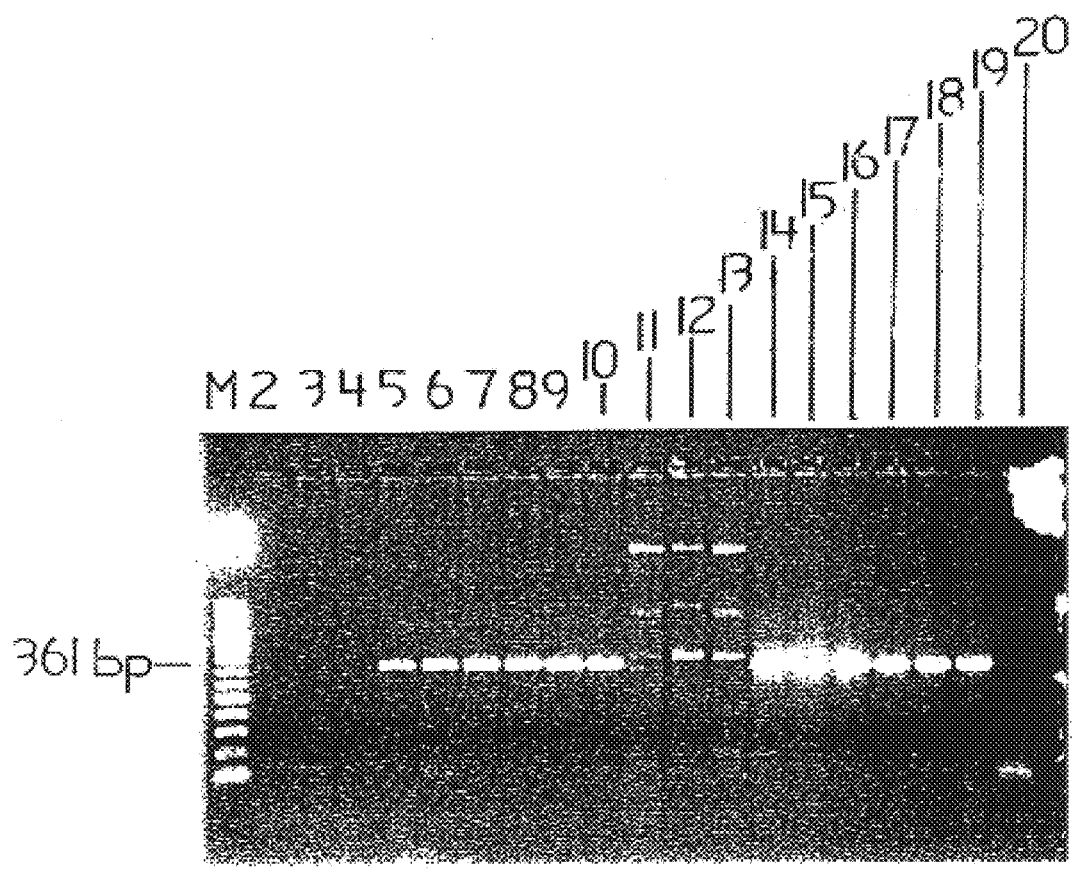
FIG. 3 is an image of a DNA gel depicting the greater amount of PCR amplification product visualized following CC-PCR compared with the amplification product resulting from PCR alone.
Figure 4:
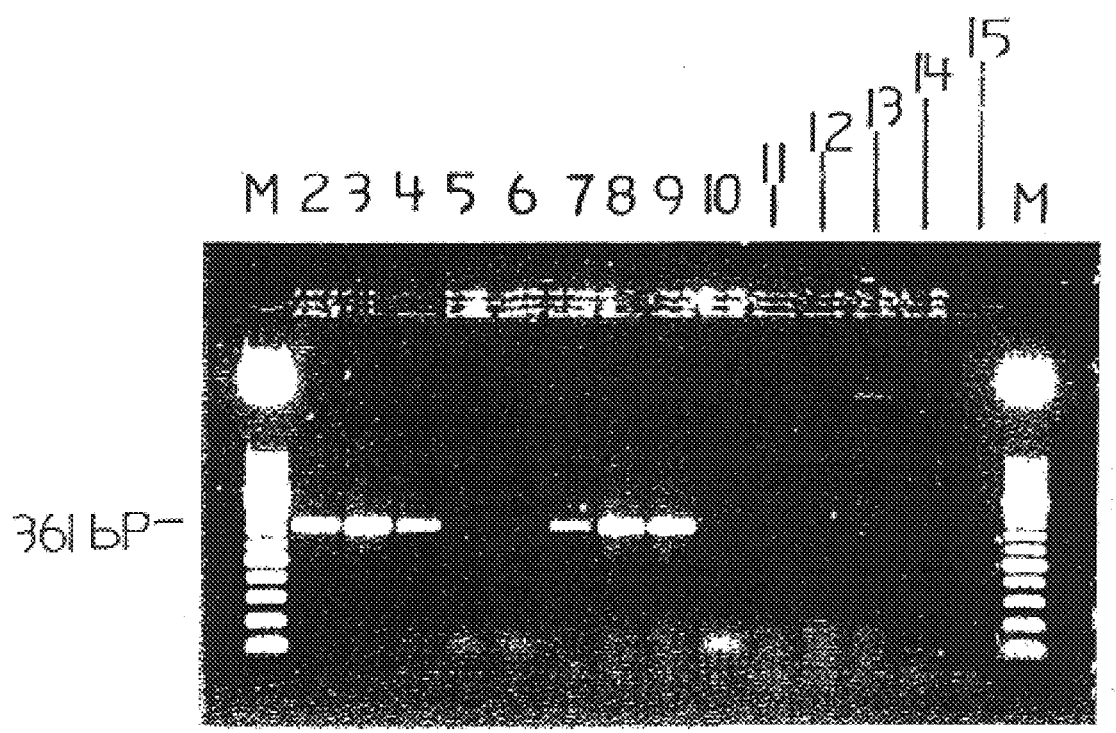
FIG. 4 is an image of a DNA gel depicting the detection of PCR amplification product following CC-PCR where the oocysts were pre-treated (untreated, acid triggered at pH 2.75 for one hour, or trypsin/sodium taurocholate excysted) prior to inoculation onto HCT-8 cells. PCR was performed using an annealing temperature of 59° C. to reduce non-specific background.

The data disclosed demonstrate possible parasite amplification in the HCT-8 cell line. That is, equivalent numbers of oocysts were used in each PCR and CC-PCR, and significantly less PCR amplification product (361 bp DNA band) was visualized for the PCR of the original inoculum compared with the PCR product detected following cell culture-PCR (FIG. 3, lanes 5–10 and 14–19, respectively). FIG. 4 is an image of a DNA gel depicting the comparison of the production of PCR amplification product by either PCR or CC-PCR on oocysts recovered by IMS. The PCR annealing temperature was 55° C. for all samples. Each water sample (raw water or raw water concentrate) was seeded with 400 oocysts, the oocysts were recovered by IMS, and the samples were divided equally. One half of the sample was used directly for PCR and the gel lanes were loaded as follows: lanes 2–4, negative control unseeded raw water; lanes 5–7, seeded raw water; lanes 8–10, seeded raw water concentrate. The other half of each sample was inoculated onto HCT-8 cells and PCR was performed after incubation of the cells for 72 hours. The gel lanes were loaded as follows: lanes 11–13, unseeded raw water; lanes 14–16, seeded raw water; lanes 17–19, seeded raw water concentrate. Lane 20 contained PCR mixture from uninfected HCT-8 cells and a lane of molecular weight standards (2,000–50 bp) is included on either side of the gel.

The data demonstrate that CC-PCR yielded more PCR amplification product than standard PCR alone. The 361 bp PCR amplification product band is much more intensely stained in the samples derived from CC-PCR (compare FIG. 3, lanes 5–10 with lanes 14–19). This was so even for a sample which had considerably lower original inoculum PCR product (FIG. 3, lanes 5 and 14, respectively).

Cell culture-PCR demonstrated some background problems associated with HCT-8 cells as demonstrated by the three bands present in lanes 11–13 for the unseeded raw water inoculum. The same unseeded raw water sample did not give any background bands when used in PCR alone (FIG. 3, lanes 2–4). The non-specific background was reduced by increasing the annealing temperature from 55° C. to 59° C. thereby increasing the hybridization stringency. Further investigation of this background phenomenon using freeze-killed oocyst controls yielded similar results (FIG. 4). One sample having 100 freeze-killed oocysts (FIG. 4, lane 7) gave a weak PCR signal most likely due to killed oocysts not washed out of the well and/or very low infection from an oocyst which survived freezing.

FIG. 4 is an image of a DNA gel visualizing the PCR amplification products of PCR following HCT-8 culture. The cells were inoculated with oocysts subjected to various treatments, i.e., the cells were inoculated with untreated oocysts, oocysts acid triggered for one hour at pH 2.75, or excysted with trypsin/taurocholate. The stated numbers of oocysts are based on an in vitro excystation frequency of 51% for the oocyst stock. The gel lanes were loaded with CC-PCR reaction samples from cell inoculated with the following inoculums: lane 2, 50 untreated oocysts; lane 3, 50 acid triggered oocysts; lane 4, 50 excysted oocysts; lane 5, 50 freeze-killed untreated oocysts; lane 6, 50 freeze-killed acid triggered oocysts; lane 7, 50 freeze-killed excysted oocysts; lane 8, 5 untreated oocysts; lane 9, 5 acid triggered oocysts; lane 10, 5 excysted oocysts; lane 11, 5 freeze-killed untreated oocysts; lane 12, 5 freeze-killed acid triggered oocysts; lane 13, 5 freeze-killed excysted oocysts. Lane 4 contained a sample of the PCR mixture of uninfected HCT-8 cell DNA, and lane 15 contained a negative control PCR mix with no template DNA. Molecular weight standards (2,000–50 bp) were loaded on either end of the gel (M).

These data demonstrate that CC-PCR has a detection limit of approximately 5 infectious oocysts, possibly lower considering infection efficiency by released sporozoites was probably less than 100%. Thus, the CC-PCR method holds great promise in meeting existing pressing need for a rapid, cost-effective assay for the detection of a single *C. parvum* oocyst recovered from environmental water concentrates.

EXAMPLE 2
Detection of Oocysts by IMS Combined with a Thermostable Intercalating Fluorescent Dye Homogeneous Format The experiments presented in this example may be summarized as follows. Oocysts were detected in environmental raw water sample concentrates (0.5 ml pellet volume) known to be negative for *C. parvum* which were seeded with either 10 or 5 oocysts. Oocyst DNA was detected using a PCR-based homogeneous format (i.e., closed-tube) assay (Qualicon, Wilmington, Del.). This assay involves tableted reagents which include a thermostable DNA intercalating fluorescent dye (SYBR green 1) which fluoresces when it intercalates into double-stranded DNA (ds-DNA) thereby allowing the formation of ds-DNA during PCR amplification to be monitored by a fluorometer. The data disclosed herein demonstrate that this simple method efficiently and selectively detects *C. parvum* oocysts without the need of an operator skilled in molecular biology techniques.

The materials and methods used in this example are as follows.

Oocyst Stocks

Purified *C. parvum* oocysts were obtained from Waterborne, Inc. (New Orleans, La.). Oocysts were lysed by eight cycles of freezing in liquid nitrogen and thawing in a 98° C. heated block. Aliquots of lysed samples were used directly for PCR without further purification.

Immunomagnetic Separation (IMS) Purification of Environmental Raw Water Samples

IMS (Dynabeads anti-Cryptosporidium, Dynal, Oslo, Norway) was used to purify environmental raw water concentrates (0.5 ml packed pellet volume) as described previously herein. The raw water concentrate used had been previously analyzed and had been found to be negative for *C. parvum* oocysts by microscopy and PCR. To evaluate any potential PCR inhibition due to IMS, the concentrates were freeze-thaw treated identical to oocyst stocks and then added to PCR master mixes seeded with known amounts of *C. parvum*.

PCR Detection of *C. parvum* Oocysts

Each 50 µl PCR mixture contained amplification buffer with magnesium, tableted PCR reagents (Qualicon, Wilmington, Del.), PCR primers specific for the *C. parvum* hsp70 gene as described in Rochelle et al. (1997, Appl. Environ. Microbiol. 63:2029–2037), and varying amounts of *C. parvum* template DNA.

PCR was performed using a model 9600 DNA thermal cycler (Perkin-Elmer, Foster City, Calif.). The amplification products were detected using a BAX™ fluorometer (Qualicon, Wilmington, Del.).

The amplification products were separated by horizontal gel electrophoresis and visualized by ethidium bromide staining to visualize the PCR amplification product (ie., a 361 bp fragment). The gel images were captured using a gel documentation system (UVP, Inc., Upland, Calif.), and the relative intensities of the ethidium bromide-stained amplification products visualized by ethidium bromide staining were compared with the BAX™ fluorometer fluorescence measurements.

The Results of the experiments are as follows.

The feasibility of using a homogeneous format PCR-based assay to detect *C. parvum* from environmental raw water samples was examined. The strategy was to use a double stranded DNA intercalating thermostable fluorescent dye (SYBR green 1) in a PCR-based assay to measure the formation of ds-DNA as an indicator that the target sequence was amplified. This enables a closed-tube assay where the reaction is performed in tubes which can be placed directly into a fluorometer thus minimizing sample handling. The specificity of the amplification product was confirmed by comparing the fluorescence results of the assay with standard techniques which visualize the amplification on ethidium bromide-stained agarose gels.

Detection Limit Using Purified Oocysts

Purified *C. parvum* oocyst stocks were used to determine the detection limit of the assay. Initial trials used five replicates of 5 and 10 oocysts per reaction. Fluorometer readings (expressed in fluorescence intensity units, FIU) revealed successful amplification in all oocyst-seeded reactions compared to no *C. parvum* template negative controls. However, endpoint fluorescence was not significantly different between the 10 and 5 oocysts levels (Table 2).

TABLE 2

| n = 10 | n = 10 | n = 10 | n = 10 | n = 10 | n = 5 | n = 5 | n = 5 | n = 5 | n = 5 |
|---|---|---|---|---|---|---|---|---|---|
| FIU 106.5 | 68.1 | 139.8 | 113.7 | 125.3 | 76.3 | 49.4 | 142.6 | 90.4 | 124.9 |

To compare PCR product detection by endpoint fluorescence to standard visual detection methods, 10 µl of each completed PCR was analyzed by agarose gel electrophoresis. The amount of C. parvum PCR product (361 bp) observed on the gel (FIG. 5) moderately agreed with the fluorescence intensity (FIU) of the sample disclosed in Table 2.

Effect of Environmental Raw Water Concentrates on PCR Detection

In order to evaluate the potential PCR-inhibition caused by raw water concentrates, IMS-purified raw water samples (from 0.5 ml packed pellets) were freeze-thaw treated identical to oocyst stocks then added to the PCR master mix seeded with the crude oocyst DNA obtained from 10 C. parvum oocysts. Fluorometer readings (FIU) revealed successful amplification of C. parvum DNA in all oocyst-seeded reactions compared to a negative control which contained IMS concentrate but which was not seeded with oocysts and contained no C. parvum DNA (Table 3).

TABLE 3

| | n = 10 | n = 10 | n = 10 | n = 10 |
|---|---|---|---|---|
| FIU | 53.9 | 29.8 | 25.4 | 11.3 |

Again, a comparison of PCR product detection by endpoint fluorescence to standard visual detection was performed, but due to the low fluorescence readings, 15 µl of each completed PCR reaction mixture were analyzed by gel electrophoresis instead of the 10 µl aliquot examined previously for purified oocysts without IMS-raw water concentrate added. The amount of C. parvum PCR product visually detected on the gel (FIG. 6) agreed poorly with the fluorescence intensity (FIU) of the sample (Table 3).

Using the disclosed strategy, the prototype C. parvum PCR detection kit appears capable of detecting as few as 5 oocysts using purified oocyst stocks and as few as 10 oocysts in the presence of IMS-purified raw water concentrates. However, signal to background ratios were considerably lower in reactions which contained IMS-purified concentrates, and it is therefore unlikely that a desirable limit of less than 5 oocysts can be obtained using IMS-purified environmental raw water samples.

Of course, all double stranded DNA is detected by this method; thus, the assay is not specific for the specific *C. parvum* target sequence. Nonetheless, this method provides a rapid and sensitive initial screen to determine the presence of *C. parvum* in a sample and represents a significant improvement over prior art methods requiring complicated processing by a technician skilled in recombinant DNA techniques.

EXAMPLE 3

Detection of Oocysts by IMS Combined with Quantitative Sequence Detection

The experiments presented in this example may be summarized as follows. The majority of prior art molecular methods for the detection of *C. parvum* oocysts employ the PCR assay. The specificity of the PCR is based on the selection of the amplification primers and the stringency of the reaction conditions. Using standard PCR methods, presumptive positives are based on the expected size of the PCR amplification product (also referred to as the amplicon).

The present invention discloses specific and sensitive processes for the detection and quantitation of intact (viable or nonviable oocysts) containing organismal DNA and infectious *C. parvum* oocysts in various water sample matrices. These methods employ, but are not limited to, immunomagnetic separation (IMS) to recover and concentrate Cryptosporidium oocysts from a variety of water sample matrices followed by the detection of *C. parvum* genomic DNA encoding the *C. parvum* heat shock protein 70 gene, i.e., hsp70 described in Khramtsov et al. (1995, J. Euk. Microbiol. 42:416–422), using the PCR assay in various formats. The use of quantitative sequence detection (QSD) of hsp70 genomic DNA allowed the determination of numbers of intact and/or infectious oocysts in a variety of water sample matrices.

*C. parvum* oocysts were detected in environmental raw water samples by concentrating the organisms using modified IMS followed by quantitative sequence detection (QSD) assay as described in Heid et al. (1996, Genome Res. 6:986–994). QSD allowed the rapid, efficient and quantitative detection of a *C. parvum*-specific amplified DNA sequence in a closed-tube assay which did not require any subsequent analysis to confirm that the amplification product was, indeed, *Cryptosporidium parvum* DNA encoding the HSP70 protein.

Further, QSD may be performed directly with intact oocysts recovered by IMS or any other concentration procedure and the concentrated oocysts may be used directly in QSD to detect total, intact oocysts in the sample. Alternatively, the concentrated sample may be used to infect a susceptible cell culture (CC-QSD) to detect viable, infectious oocysts without the need to heat shock the samples, perform reverse-transcriptase assays, or conduct DNA fragment size determinations to confirm the identity of the PCR amplification product. Therefore, QSD represents significant improvements over the prior art which requires extensive manipulation of samples and which is not quantitative (see Table 4, comparing the various prior art PCR-based methods to the claimed QSD method). Therefore, the methods disclosed herein combine the advantages of a modified IMS with the ease and quantitative capacity of QSD to detect *C. parvum* in water samples.

The materials and methods used in this example are as follows.

Oocysts and Cell Culture

Oocysts and tissue culture of oocysts on HCT-8 cells were performed as described previously in Example 1 herein.

Standard PCR and CC-PCR

To detect intact oocysts, DNA obtained from freeze/thaw lysates of IMS-recovered oocysts was used directly in standard PCR as described previously herein. For detection of infectious oocysts, DNA obtained from HCT-8 cell harvests 72 hours-post-inoculation with IMS-recovered oocysts was used in CC-PCR as described previously herein. The primer pair SEQ ID NO:2 and SEQ ID NO:3 specific for the *C. parvum* hsp70 gene was used. This primer set yields a 346 bp PCR product from *C. parvum* template DNA. Additionally, the primer pair of the '368 patent ([SEQ ID NO:5] and [SEQ ID NO:6]), which specifies a 361 bp amplification product, was used and compared to the primer pair [SEQ ID NO:2] and [SEQ ID NO:3].

Each 50 µl PCR mixture contained 5 µl of 10× amplification buffer with magnesium (Boehringer Mannheim, Indianapolis, Ind.), 1 µl of a 10 mM mix of dATP, dTTP, dCTP, dGTP (10 mM each) (Boehringer Mannheim, Indianapolis, Ind.), 10 pmol of each of forward ([SEQ ID NO:2]) and reverse ([SEQ ID NO:3]) PCR primer, and 2.5 µl of 30 mg/ml BSA. The reaction mixture was overlaid with sterile mineral oil and the PCR was performed using a Perkin-Elmer model 480 or 9600 DNA thermal cycler. The amplification conditions were as follows: initial denaturation was at 95° C. for 5 minutes, the samples were held at 80° C. while 2.0 U Taq DNA polymerase (Boehringer Mannheim, Indianapolis, Ind.) was added "hot start," 40 cycles of denaturation at 94° C. for 30 seconds, annealing for 1 minute at 60° C., and extension at 72° C. for 30 seconds were performed. The 40 cycles were followed by a single extension at 72° C. for 10 minutes and a 4° C. soak to stop the reaction.

The amplification products were separated by horizontal gel electrophoresis on a 2.0% agarose (Amresco, Solon, Ohio) gel containing 0.5 µg/ml ethidium bromide (Sigma Chem. Co., St. Louis, Mo.) and the DNA was visualized under UV light. The gel images were captured using a gel documentation system (UVP, Inc., Upland, Calif.). The PCR products were cloned using a TOPO TA cloning kit (Invitrogen, Carlsbad, Calif.), sequenced by a commercial laboratory (ACGT, Northbrook, Ill.), and sequence homology to the *C. parvum* hsp70 (GenBank Acc. No. U11761) was confirmed.

Quantitative Sequence Detection

DNA obtained from intact oocysts was obtained by freeze-thaw lysis and used directly for QSD for quantitation of intact oocysts. Alternatively, for the quantitation of infectious oocysts, DNA obtained from HCT-8 cell harvests was used for QSD (i.e., CC-QSD).

QSD was performed as described in Heid et al. (1996, Genome Res. 6:986–994). In essence, the QSD primer pair ([SEQ ID NO:2 and SEQ ID NO:3]) specific for the *C. parvum* hsp70 DNA and the amplification product specific internal fluorogenic TaqMan™ oligonucleotide probe [SEQ ID NO:4] labeled 5' with 6-carboxyfluorescein (6-FAM) and 3' with 6-carboxytetramethylrhodamine (TAMRA) were used. Similarly, primer pair ([SEQ ID NO:5 and SEQ ID NO:6]) and TaqMan™ oligonucleotide probe [SEQ ID NO:7] were also prepared and used for QSD. All probes and primers were chemically synthesized and were obtained from commercial sources (Synthegen, Houston, Tex.).

Each 50 µl QSD mixture contained 5 µl of 10 amplification buffer with Mg (1.5 mM final, Perkin-Elmer); 0.5 µl of a 20 mM mix of each DATP, dTTP, dCTP, dGTP; 10.0 pmol of each forward and reverse primers and internal quencher-fluorescer probe; and 2.5 µl of 30 mg/ml BSA; 2.5 U of DNA polymerase; and nucleic acid template.

QSD was performed using a Perkin-Elmer Applied Biosystems 7700 Sequence Detector with the following cycling conditions: initial denaturation for 15 minutes at 95° C., followed by 40 to 60 cycles of denaturation at 95° C. for 30 seconds and anneal/extension at 60° C. for 1 minute (Table 5). Automated data analysis was performed after completion of the reactions by the sequence detection software provided with the instrument per the manufacturer's instructions.

The results of the experiments are as follows.

Detection of QSD Amplification Product

During QSD, the internal *C. parvum* hsp70 gene fluorescer-quencher oligonucleotide probe ([SEQ ID NO:4] and SEQ ID NO:7]) hybridizes to the complementary amplified sequence between the forward primer sequence ([SEQ ID NO:2] and [SEQ ID NO:5]) and the reverse primer sequence ([SEQ ID NO:3] and [SEQ ID NO:6]). When the oligonucleotide probe is intact, the reporter fluorescence is quenched by the quencher molecule. However, once the 5'→3' exonuclease activity of the Taq DNA polymerase cleaves the fluorescer reporter away from the rest of the probe, the reporter fluorescence at 518 nm is no longer quenched and can be measured by a CCD camera connected to the assay tube containing the reaction mixture. The assay tube also has a laser connected to it by fiber optics. Thus, the 7700 Sequence Detector allows measurement of the changes in fluorescence in "real time" during the PCR cycling reaction as the target nucleic acid is being amplified without the need to remove the samples or open the tube. Further, unlike standard PCR, presence of the probe in the reaction mixture during QSD allows the fluorescence to be measured after each round of amplification and data may be gathered during the assay. Comparison of QSD with other PCR-based *C. parvum* Detection Assays A comparison of the various PCR-based assays for detection of *C. parvum* in water samples is set forth in Table 4. Quantitative sequence detection provides the quickest assay (only one day) to detect intact *C. parvum* in a sample. Further, QSD with integrated cell culture (CC-QSD) is the fastest assay for detection of infectious *C. parvum* in a sample. This is because, as previously explained herein, QSD does not require agarose gel DNA size fractionation followed by Southern blot or sequencing to confirm the specificity of the PCR results. More importantly, as more fully discussed below, only QSD provides a quantitative measure of the number of intact and/or infectious oocysts in the sample whereas the other PCR-based methods do not.

TABLE 4

| Method | Target Nucleic Acid | Type of Oocysts detected | Procedure for Confirmation of specificity of amplification | Time of sample processing, assay and confirmation |
|---|---|---|---|---|
| Standard PCR | DNA | viable and nonviable | Internal probe hybridization | 2–3 days |
| RT-PCR | mRNA | viable | Internal probe hybridization | 2–3 days |
| Integrated cell culture PCR (CC-PCR) | DNA or mRNA | infectious/ viable | Internal probe hybridization | 4–6 days |
| Quantitative sequence detection (QSD) | DNA mRNA | viable/ nonviable viable only | 5' nuclease fluorogenic probe in reaction | 1 day |
| Nucleic acid sequence-based amplification (NASBA) | mRNA | viable | fluorescent molecular beacon probe in reaction | 1 day |
| Integrated cell culture QSD or NASBA | DNA or mRNA | infectious | same as above for QSD and NASBA | 2–3 days |

Comparison of Claimed QSD with QSD Performed Using Prior Art Primers

As discussed previously herein, the design of the primers and the probe to be used in PCR and QSD based assays is crucial to the specificity and sensitivity of the method. In order to maximize the efficiency of primers and probes for QSD detection of *C. parvum*, novel primers and probes were designed and compared to those disclosed previously by De Leon and Rochelle, 1998, U.S. Pat. No. 5,770,368. The results of comparison experiments are shown in FIGS. 7A and 7B. The '368 patent primers and probes were used to detect *C. parvum* in water samples seeded with known numbers of oocysts, i.e., 4000, 400, or 40 oocysts (FIG. 7A). Although the primers and probes were somewhat quantitative, the change in normalized reporter signal ($\Delta R_n$) rapidly became variable with some samples containing 4,000 oocysts demonstrating a lower $\Delta R_n$ than samples containing 400 oocysts during the exponential phase of amplification (FIG. 7A). Further, the threshold cycle for each standard. was more clearly defined for reactions using the claimed primer pair and oligonucleotide TaqMan™ probe thus yielding a more accurate standard curve to be used to quantify oocysts in unknown samples (FIG. 7C).

QSD using the preferred primers and probe (i.e., [SEQ ID NO:2] and [SEQ ID NO:3]), however, demonstrated a correlation between the change in normalized reporter signal ($\Delta R_n$) and the number of oocysts in the sample which persisted beyond 46 amplification cycles (FIG. 7B). Further, the preferred primers and probe yielded a much higher change in normalized reporter signal with values for standards containing 4,000 oocysts exceeding 0.4 after only 40 cycles while the $\Delta R_n$ for standards containing 4,000 oocysts using the '368 patent primers and probe were less than 0.25 after 40 cycles. Moreover, the preferred primers and probe permitted the generation of a QSD standard curve (FIG. 7C) computed by plotting the threshold cycle (CT) as a function of starting target DNA quantity. This standard curve permitted the quantitation of the number of oocysts present in four unknown samples (FIG. 7C and Table 5).

TABLE 5

Thermal Cycle Conditions

| Cycle | Temperature | Time | Repeat | Ramp Time | Auto Increment |
|---|---|---|---|---|---|
| Hold | 95° C. | 15:00 | | Auto | |
| Cycle | 95° C. | 0:30 | 60 | Auto | |
| | 60° C. | 1:00 | | Auto | |
| Cycle | 72° C. | 10:00 | 1 | Auto | |
| Cycle | 4° C. | 95:00 | 99 | Auto | |

Standard Curve

| | |
|---|---|
| Slope: −5.41 | Threshold: 0.04 |

TABLE 5-continued

| | |
|---|---|
| Intercept: 51.49 | Baseline Range: (3, 15) |

Sample Information

| Well | Type | Sample Name | Replicate | Ct | Quantity | Std. Dev. | Mean |
|---|---|---|---|---|---|---|---|
| A1 | STND | A1 | | 32.40 | 4.0e+03 | 0.00 | 4000.00 |
| A2 | STND | A2 | | 32.05 | 4.0e+03 | 0.00 | 4000.00 |
| A3 | STND | A3 | | 32.04 | 4.0e+03 | 0.00 | 4000.00 |
| A4 | STND | A4 | | 31.25 | 4.0e+03 | 0.00 | 4000.00 |
| A5 | STND | A5 | | 31.94 | 4.03+03 | 0.00 | 4000.00 |
| A6 | STND | A6 | | 31.50 | 4.0e+03 | 0.00 | 4000.00 |
| B1 | STND | B1 | | 37.17 | 4.0e+02 | 0.00 | 400.00 |
| B2 | STND | B2 | | 37.40 | 4.0e+02 | 0.00 | 400.00 |
| B3 | STND | B3 | | 37.41 | 4.0e+02 | 0.00 | 400.00 |
| B4 | STND | B4 | | 38.07 | 4.0e+02 | 0.00 | 400.00 |
| B5 | STND | B5 | | 38.05 | 4.0e+02 | 0.00 | 400.00 |
| B6 | STND | B6 | | 38.08 | 4.0e+02 | 0.00 | 400.00 |
| C1 | UNKN | C1 | | 45.64 | 1.2e+01 | 0.00 | 12.06 |
| C2 | UNKN | C2 | | 40.52 | 1.1e+02 | 0.00 | 106.86 |
| C3 | UNKN | C3 | | 42.07 | 5.5e+01 | 0.00 | 55.13 |
| C4 | UNKN | C4 | | 39.83 | 1.4e+02 | 0.00 | 143.33 |
| C5 | STND | C5 | | 41.99 | 4.0e+01 | 0.00 | 40.00 |
| C6 | STND | C6 | | 42.82 | 4.0e+01 | 0.00 | 40.00 |
| E2 | NTC | E2 | NTC | 60.00 | | 0.00 | 0.00 |
| E3 | NTC | E3 | NTC | 60.00 | | 0.00 | 0.00 |
| E4 | NTC | E4 | NTC | 60.00 | | 0.00 | 0.00 |
| E5 | NTC | E5 | NTC | 60.00 | | 0.00 | 0.00 |

Therefore, QSD permitted quantitation of the actual number of *C. parvum* oocysts in a starting sample based on fluorescence measurements detected in "real time" fashion using the preferred primer set and fluorescer-quencher oligonucleotide probe. Standard PCR, on the other hand, does not permit quantitation of starting amount of target DNA and requires several additional days of sample processing since the identity of the PCR product must be confirmed by Southern blotting and/or sequencing analysis.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method useful for detecting a *Cryptosporidium parvum* organism in an aqueous sample, the method comprising
    (a) concentrating any *Cryptosporidium parvum* organism present in the sample by immunomagnetic separation;
    (b) amplifying a target *Cryptosporidium parvum* nucleic acid present in the sample using a nucleic acid selected from the group consisting of a nucleic acid having the sequence SEQ ID NO:2 and a nucleic acid having the sequence SEQ ID NO:3, and
    (c) detecting any amplified target nucleic acid formed in step (b) thereby detecting a *Cryptosporidium parvum* organism in an aqueous sample;
    wherein the detection of step (c) comprises using an oligonucleotide probe having the sequence SEQ ID NO:4.

2. The method of claim 1, wherein the aqueous sample is selected from the group consisting of an environmental raw water sample, a backwash water sample, a process water sample, and a finished water sample.

3. The method of claim 1, further comprising infecting a susceptible mammalian cell culture with a *Cryptosporidium parvum* organism concentrated in step (a), and producing the *Cryptosporidium parvum* target nucleic acid prior to amplifying the target nucleic acid in step (b).

4. The method of claim 3, wherein the mammalian cell culture is selected from the group consisting of a HCT-8 cell culture, a CaCo-2 cell culture, and a MDBK cell culture.

5. The method of claim 3, wherein the cell culture is incubated for a period of time from about 4 hours to about 72 hours following inoculation.

6. The method of claim 1, wherein step (b) further comprises hybridizing any amplified target nucleic acid formed with a fluorescer-quencher oligonucleotide probe specific for said target *Cryptosporidium parvum* nucleic acid and measuring the level of fluorescence in the sample, wherein the level of fluorescence is quantitatively correlated to an amount of *Cryptosporidium parvum* oocysts in the sample.

7. The method of claim 6, wherein the fluorescer molecule is attached to the 5' end of the oligonucleotide probe, and further wherein the fluorescer molecule is selected from the group consisting of a 6-carboxyfluorescein fluorescer molecule, a tetrachloro-6-carboxyfluorescein fluorescer molecule, a 2,7-dimethoxy-4,5-dichloro-6-carboxyfluorescein fluorescer molecule, and a hexachloro-6-carboxyfluorescein fluorescer molecule.

8. The method of claim 7, wherein the quencher molecule 6-carboxytetramethylrhodamine is attached to the 3' end of the oligonucleotide probe.

9. A method useful for quantitatively detecting a *Cryptosporidium parvum* organism in a sample, said method comprising
    (a) concentrating any *Cryptosporidium parvum* organism in the sample by immunomagnetic separation;
    (b) amplifying a target *Cryptosporidium parvum* nucleic acid using a nucleic acid having a sequence selected from the group consisting of SEQ ID NO:2 and SEQ ID NO:3;
    (c) hybridizing any amplified target nucleic acid formed in step (b) with a fluorescer-quencher oligonucleotide probe specific for the target *Cryptosporidium parvum* nucleic acid; and
    (d) detecting any amplified target nucleic acid by quantitative sequence detection, wherein the level of fluorescence is correlated to the quantitative measure of an amount of *Cryptosporidium parvum* oocysts in the sample, thereby quantitatively detecting a *Cryptosporidium parvum* organism in a sample.

10. The method of claim 9, wherein the nucleic acid is DNA.

11. The method of claim 9, wherein the oligonucleotide probe has the sequence SEQ ID NO:4.

12. A method of quantitatively detecting a *Cryptosporidium parvum* organism in an aqueous sample, said method comprising
    (a) contacting a target *Cryptosporidium parvum* nucleic acid with polymerase chain reaction reagents specific for the target nucleic acid, the polymerase chain reaction reagents including a polymerase chain reaction primer selected from the group consisting of a primer having the sequence SEQ ID NO:2 and a primer having the sequence SEQ ID NO:3, a polymerase enzyme, and an oligonucleotide probe, wherein the oligonucleotide probe further comprises:
        (i) a sequence that hybridizes to a portion of the target *Cryptosporidium parvum* nucleic acid wherein the portion is unique to *Cryptosporidium parvum;*
        (ii) a fluorescer molecule attached to a 5' end of the oligonucleotide probe;
        (iii) a quencher molecule attached to a 3' end of said oligonucleotide probe capable of substantially quenching the fluorescer molecule when the oligonucleotide probe is intact, wherein the fluorescer molecule becomes substantially unquenched when the oligonucleotide probe is cleaved by DNA polymerase during amplification of the *Cryptosporidium parvum* target nucleic acid; and
        (iv) a 3' end which is impervious to the 5'→3' extension activity of the DNA polymerase;
    (b) amplifying the target *Cryptosporidium parvum* nucleic acid by thermal cycling, wherein the thermal cycling is sufficient to amplify the target nucleic acid; and
    (c) measuring the level of fluorescence in the sample subsequent to thermal cycling, and further wherein the level of fluorescence is correlated to an amount of *Cryptosporidium parvum* oocysts present in the sample, thereby quantitatively detecting a *Cryptosporidium parvum* organism in an aqueous sample.

13. The method of claim 12, wherein the aqueous sample is selected from the group consisting of an environmental raw water sample, a backwash water sample, a process water sample, and a finished water sample.

14. The method of claim 12, further comprising concentrating any *Cryptosporidium parvum* organism present in the sample using immunomagnetic separation prior to step (a).

15. The method of claim 14, further comprising infecting a susceptible mammalian cell culture with any *Cryptosporidium parvum* organism concentrated by immunomagnetic separation and producing the *Cryptosporidium parvum* target nucleic acid prior to step (a).

16. The method of claim 12, wherein the oligonucleotide probe has the sequence SEQ ID NO:4.

17. A method useful for detecting a *Cryptosporidium parvum* organism in an aqueous sample, the method comprising:

amplifying a target *Cryptosporidium parvum* nucleic acid present in the sample using a nucleic acid selected from the group consisting of a nucleic acid having the sequence SEQ ID NO:2 and a nucleic acid having the sequence SEQ ID NO:3; and detecting any amplified target nucleic acid formed thereby detecting a *Cryptosporidium parvum* organism in an aqueous sample.

18. The method of claim 17, the method further comprising concentrating any *Cryptosporidium parvum* present in the sample.

19. The method of claim 17, the method further comprising detecting the amplified target nucleic acid using an oligonucleotide probe having the sequence SEQ ID NO:4.

20. A kit for detecting a *C. parvum* nucleic acid, the kit comprising a nucleic acid selected from the group consisting of a nucleic acid having the sequence SEQ ID NO:2, a nucleic acid having the sequence SEQ ID NO:3, and a nucleic acid having the sequence SEQ ID NO:4.

21. An isolated nucleic acid having the sequence SEQ ID NO:2.

22. An isolated nucleic acid having the sequence SEQ ID NO:3.

23. An isolated nucleic acid having the sequence SEQ ID NO:4.

* * * * *

SEQUENCE LISTING

```
<160> NUMBER OF SEQ ID NOS:  7

<210> SEQ ID NO 1
<211> LENGTH: 2800
<212> TYPE: DNA
<213> ORGANISM: Cryptosporidium parvum
<220> FEATURE:
<223> OTHER INFORMATION: partial sequence for t he heat shock protein 70
      gene

<400> SEQUENCE: 1
```

-continued

| | |
|---|---|
| agagaaagaa tagaggtatg gatttaacca caaatgctag agctttaaga a gactcagaa | 60 |
| ctcaatgcga gcgtgcaaag agaactttgt catcttctac tctctttctt a tctccatac | 120 |
| ctaaattggt gtttacgatc tcgaaattct tctgagtctt gagttacgct c gcacgtttc | 180 |
| tcttgaaaca gtagaagatg tcaagctaca attgagttag attcactcta t gaaggtatt | 240 |
| gattattcag ttgccatcag tagagctaga ttcgaagaac tctgcgctga t tacttccgt | 300 |
| agttcgatgt taactcaatc taagtgagat acttccataa ctaataagtc a acggtagtc | 360 |
| atctcgatct aagcttcttg agacgcgact aatgaaggca gcaactttag c tccagttga | 420 |
| gaaagtactc aaggatgctg gtatggacaa gagatctgta catgatgttg t attggttgg | 480 |
| tggttctaca cgtattccaa cgttgaaatc gaggtcaact cttcatgag t tcctacgac | 540 |
| catacctgtt ctctagacat gtactacaac ataaccaacc accaagatgt g cataaggtt | 600 |
| aggttcaggc cttgattcag gaattcttta acggtaaaga gccatgcaaa g caatcaatc | 660 |
| cagacgaagc tgttgcttat ggtgctgctg tacaagctgc tccaagtccg g aactaagtc | 720 |
| cttaagaaat tgccatttct cggtacgttt cgttagttag gtctgcttcg a caacgaata | 780 |
| ccacgacgac atgttcgacg tatcttaaat ggtgagcaat cctctgccgt a caggatctc | 840 |
| ttattattgg atgttgctcc attatcactc ggtttagaaa ctgctggtgg t gttatgacc | 900 |
| atagaattta ccactcgtta ggagacggca tgtcctagag aataataacc t acaacgagg | 960 |
| taatagtgag ccaaatcttt gacgaccacc acaatactgg aagcttattg a acgtaatac | 1020 |
| aactatccca gcaaagaaga cacaagtctt cactacttat gctgataacc a gagtggtgt | 1080 |
| cttgatccaa gtttatgagg ttcgaataac ttgcattatg ttgatagggt c gtttcttct | 1140 |
| gtgttcagaa gtgatgaata cgactattgg tctcaccaca gaactaggtt c aaatactcc | 1200 |
| gtgagagagc catgactaag gataaccatc tcctcggaaa gttccatctt g atggtattc | 1260 |
| caccagcacc aagaggtgta ccacaaattg aagtcaccct cactctctcg g tactgattc | 1320 |
| ctattggtag aggagccttt caaggtagaa ctaccataag gtggtcgtgg t tctccacat | 1380 |
| ggtgtttaac ttcagtggaa tgatattgat gctaatggta tcttgaatgt g tctgctgtt | 1440 |
| gataagagta ctggtaagag cagcaagatc actattacta acgataaggg t agattatca | 1500 |
| actataacta cgattaccat agaacttaca cagacgacaa ctattctcat g accattctc | 1560 |
| gtcgttctag tgataatgat tgctattccc atctaatagt aacgatattg a acgtatggt | 1620 |
| taatgatgct gagaaataca agggtgagga tgagcagaac agacttaaga t tgaggctaa | 1680 |
| gaactctttg gagaactacc ttgctataac ttgcatacca attactacga c tctttatgt | 1740 |
| tcccactcct actcgtcttg tctgaattct aactccgatt cttgagaaac c tcttgatgg | 1800 |
| tctataacat gaggaacacc atccaagaac caaaggttaa ggaaaagctt t ctcaatctg | 1860 |
| aaattgatga ggctgagaag aagatcaagg atgctcttga agatattgta c tccttgtgg | 1920 |
| taggttcttg gtttccaatt ccttttcgaa agagttagac tttaactact c cgactcttc | 1980 |
| ttctagttcc tacagaaact ctggctcgag cacaaccaaa ctgctgaaaa g gacgagttt | 2040 |
| gaacatcaac aaaaggagat tgaaactcat atgaatccac tcatgatgaa g atctactct | 2100 |
| gaccgagctc gtgttggttt gacgactttt cctgctcaaa cttgtagttg t tttcctcta | 2160 |
| actttgagta tacttaggtg agtactactt ctagatgaga gctgagggtg g tatgccagg | 2220 |
| tggaatgcca ggtggtatgc caggcggtat gccaggtgga atgccaggtg g tatgccagg | 2280 |
| tggaatgcca ggcggtatgc cgactcccac catacggtcc accttacggt c caccatacg | 2340 |
| gtccgccata cggtccacct tacggtccac catacggtcc accttacggt c cgccatacg | 2400 |

```
caggtggtat gccaggtggt atgccaggtg gtatgccagg atctaatggt c caactgttg    2460 aagaggtcga ctaattattt tagtcaccaa aaaaactcac gtccaccata c ggtccacca    2520 tacggtccac catacggtcc tagattacca ggttgacaac ttctccagct g attaataaa    2580 atcagtggtt tttttgagtg tcaaaatgga agttaagaa ctatttacac a ctttcaatt    2640 tctagttatt ttttaccaaa ataagaagaa aagcacactc tacctttagg c tatattttc    2700 agttttacct ttcaattctt gataaatgtg tgaaagttaa agatcaataa a aaatggttt    2760 tattcttctt ttcgtgtgag atggaaatcc gatataaaag                          2800

<210> SEQ ID NO 2
<211> LENGTH: 24
<212> TYPE: DNA
<213> ORGANISM: Cryptosporidium parvum
<220> FEATURE:
<223> OTHER INFORMATION: forward primer

<400> SEQUENCE: 2
tcctctgccg tacaggatct ctta                                             24

<210> SEQ ID NO 3
<211> LENGTH: 26
<212> TYPE: DNA
<213> ORGANISM: Cryptosporidium parvum
<220> FEATURE:
<223> OTHER INFORMATION: reverse primer

<400> SEQUENCE: 3
tgctgctctt accagtactc ttatca                                           26

<210> SEQ ID NO 4
<211> LENGTH: 27
<212> TYPE: DNA
<213> ORGANISM: Cryptosporidium parvum
<220> FEATURE:
<223> OTHER INFORMATION: probe

<400> SEQUENCE: 4
tgttgctcca ttatcactcg gtttaga                                          27

<210> SEQ ID NO 5
<211> LENGTH: 20
<212> TYPE: DNA
<213> ORGANISM: Cryptosporidium parvum
<220> FEATURE:
<223> OTHER INFORMATION: forward primer

<400> SEQUENCE: 5
aaatggtgag caatcctctg                                                  20

<210> SEQ ID NO 6
<211> LENGTH: 20
<212> TYPE: DNA
<213> ORGANISM: Cryptosporidium parvum
<220> FEATURE:
<223> OTHER INFORMATION: reverse primer

<400> SEQUENCE: 6
cttgctgctc ttaccagtac                                                  20

<210> SEQ ID NO 7
<211> LENGTH: 20
<212> TYPE: DNA
```

```
-continued

<213> ORGANISM: Cryptosporidium parvum
<220> FEATURE:
<223> OTHER INFORMATION: probe

<400> SEQUENCE: 7
ccattatcac tcggtttaga                                              20
```